United States Patent
Jafari et al.

(10) Patent No.: US 11,235,114 B2
(45) Date of Patent: *Feb. 1, 2022

(54) METHODS AND SYSTEMS FOR LEAK ESTIMATION

(71) Applicant: Covidien LP, Mansfield, MA (US)

(72) Inventors: Mehdi M. Jafari, Laguna Hills, CA (US); Periagounder R. Arul, Irvine, CA (US); Jeffrey K. Aviano, Escondido, CA (US)

(73) Assignee: Covidien LP, Mansfield, MA (US)

( * ) Notice: Subject to any disclaimer, the term of this patent is extended or adjusted under 35 U.S.C. 154(b) by 396 days.

This patent is subject to a terminal disclaimer.

(21) Appl. No.: 16/242,260

(22) Filed: Jan. 8, 2019

(65) Prior Publication Data
US 2019/0134328 A1 May 9, 2019

Related U.S. Application Data

(60) Continuation of application No. 15/593,611, filed on May 12, 2017, now Pat. No. 10,207,068, which is a
(Continued)

(51) Int. Cl.
*A61M 16/00* (2006.01)
*A61M 16/08* (2006.01)
*A61M 16/20* (2006.01)

(52) U.S. Cl.
CPC .... *A61M 16/0063* (2014.02); *A61M 16/0051* (2013.01); *A61M 16/026* (2017.08);
(Continued)

(58) Field of Classification Search
CPC .......... A61M 2205/15; A61M 2205/50; A61M 16/0063; A61M 16/026; A61M 16/0883;
(Continued)

(56) References Cited

U.S. PATENT DOCUMENTS 3,805,780 A 4/1974 Cramer et al.
3,941,124 A 3/1976 Rodewald et al.
(Continued)

FOREIGN PATENT DOCUMENTS

DE 19808543 A1 11/1998
EP 0425092 A 5/1991
(Continued)

OTHER PUBLICATIONS

Jafari, M. et al., "Robust Feedback Design for Proportional Assist Ventilation-System Dynamics and Problem Definition" Decision and Control, 2005 and 2005 European Control Conference. CDC-E CC '05. 44th IEEE Conference on Seville, Spain Dec. 12-15, 2005 (Dec. 12, 2005), pp. 4839-4844, XP010884460 DISBN: 978-0-7803-9567-1, the whole document.
(Continued)

*Primary Examiner* — Victoria Murphy

(57) ABSTRACT

The systems and methods include providing, displaying, and/or utilizing leak estimation during ventilation of a patient with a ventilator. The systems and methods include providing, displaying, and/or utilizing internal leak estimation, total leak estimation, and/or external leak estimation during ventilation of a patient with a ventilator.

19 Claims, 4 Drawing Sheets

Related U.S. Application Data division of application No. 14/057,610, filed on Oct. 18, 2013, now Pat. No. 9,675,771.

(52) U.S. Cl.
CPC .... *A61M 16/0833* (2014.02); *A61M 16/0875* (2013.01); *A61M 16/0883* (2014.02); *A61M 16/20* (2013.01); *A61M 2016/0027* (2013.01); *A61M 2016/0033* (2013.01); *A61M 2016/0039* (2013.01); *A61M 2016/0042* (2013.01); *A61M 2202/025* (2013.01); *A61M 2202/0208* (2013.01); *A61M 2205/15* (2013.01); *A61M 2205/3331* (2013.01); *A61M 2205/50* (2013.01); *A61M 2205/505* (2013.01); *A61M 2230/06* (2013.01); *A61M 2230/205* (2013.01); *A61M 2230/42* (2013.01)

(58) Field of Classification Search
CPC .............. A61M 16/0875; A61M 16/20; A61M 16/0833; A61M 16/0051; A61M 2016/0033; A61M 2205/3331; A61M 2202/0208; A61M 2202/025; A61M 2205/505; A61M 2230/06; A61M 2230/205; A61M 2230/42; A61M 2016/0027; A61M 2016/0039; A61M 2016/0042

See application file for complete search history.

(56) References Cited

U.S. PATENT DOCUMENTS

| | | |
|---|---|---|
| 4,056,098 A | 11/1977 | Michel et al. |
| 4,305,388 A | 12/1981 | Brisson |
| 4,340,044 A | 7/1982 | Levy et al. |
| 4,448,192 A | 5/1984 | Stawitcke et al. |
| 4,752,089 A | 6/1988 | Carter |
| 4,766,894 A | 8/1988 | Legrand et al. |
| 4,921,642 A | 5/1990 | LaTorraca |
| 4,939,647 A | 7/1990 | Clough et al. |
| 4,954,799 A | 9/1990 | Kumar |
| 4,971,052 A | 11/1990 | Edwards |
| 4,972,842 A | 11/1990 | Korten et al. |
| 4,986,268 A | 1/1991 | Tehrani |
| 5,057,822 A | 10/1991 | Hoffman |
| 5,072,728 A | 12/1991 | Pasternack |
| 5,072,737 A | 12/1991 | Goulding |
| 5,094,235 A | 3/1992 | Westenskow et al. |
| 5,148,802 A | 9/1992 | Sanders et al. |
| 5,150,291 A | 9/1992 | Cummings et al. |
| 5,161,525 A | 11/1992 | Kimm et al. |
| 5,237,987 A | 8/1993 | Anderson et al. |
| 5,239,995 A | 8/1993 | Estes et al. |
| 5,259,373 A | 11/1993 | Gruenke et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,313,937 A | 5/1994 | Zdrojkowski et al. |
| 5,315,989 A | 5/1994 | Tobia |
| 5,316,009 A | 5/1994 | Yamada |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,365,922 A | 11/1994 | Raemer |
| 5,368,019 A | 11/1994 | LaTorraca |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,492,113 A | 2/1996 | Estes et al. |
| 5,503,146 A | 4/1996 | Froehlich et al. |
| 5,503,147 A | 4/1996 | Bertheau |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,551,418 A | 9/1996 | Estes et al. |
| 5,551,419 A | 9/1996 | Froehlich et al. |
| 5,555,880 A | 9/1996 | Winter et al. |
| 5,596,984 A | 1/1997 | O'Mahoney et al. |
| 5,598,838 A | 2/1997 | Servidio et al. |
| 5,605,151 A | 2/1997 | Lynn |
| 5,623,923 A | 4/1997 | Bertheau et al. |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,645,053 A | 7/1997 | Remmers et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,685,296 A | 11/1997 | Zdrojkowski et al. |
| 5,687,715 A | 11/1997 | Landis et al. |
| 5,692,497 A | 12/1997 | Schnitzer et al. |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,876,352 A | 3/1999 | Weismann |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,891,023 A | 4/1999 | Lynn |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,927,274 A | 7/1999 | Servidio et al. |
| 5,934,274 A | 8/1999 | Merrick et al. |
| 5,970,975 A | 10/1999 | Estes et al. |
| 6,024,089 A | 2/2000 | Wallace et al. |
| 6,029,664 A | 2/2000 | Zdrojkowski et al. |
| 6,041,780 A | 3/2000 | Richard et al. |

(56) References Cited

U.S. PATENT DOCUMENTS

| | | |
|---|---|---|
| 6,047,860 A | 4/2000 | Sanders |
| 6,055,981 A | 5/2000 | Laswick et al. |
| 6,076,523 A | 6/2000 | Jones et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,123,074 A | 9/2000 | Hete et al. |
| 6,135,106 A | 10/2000 | Dirks et al. |
| 6,142,150 A | 11/2000 | O'Mahony et al. |
| 6,148,814 A | 11/2000 | Clemmer et al. |
| 6,152,129 A | 11/2000 | Berthon-Jones |
| 6,158,432 A | 12/2000 | Biondi et al. |
| 6,161,539 A | 12/2000 | Winter |
| 6,220,245 B1 | 4/2001 | Takabayashi et al. |
| 6,223,064 B1 | 4/2001 | Lynn et al. |
| 6,253,765 B1 | 7/2001 | Högnelid et al. |
| 6,257,234 B1 | 7/2001 | Sun |
| 6,269,812 B1 | 8/2001 | Wallace et al. |
| 6,273,444 B1 | 8/2001 | Power |
| 6,279,569 B1 | 8/2001 | Berthon-Jones |
| 6,283,119 B1 | 9/2001 | Bourdon |
| 6,286,508 B1 | 9/2001 | Remmers et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,342,039 B1 | 1/2002 | Lynn et al. |
| 6,349,724 B1 | 2/2002 | Burton |
| 6,357,438 B1 | 3/2002 | Hansen |
| 6,360,741 B2 | 3/2002 | Truschel |
| 6,360,745 B1 | 3/2002 | Wallace et al. |
| 6,369,838 B1 | 4/2002 | Wallace et al. |
| 6,371,114 B1 | 4/2002 | Schmidt et al. |
| 6,390,091 B1 | 5/2002 | Banner et al. |
| 6,412,483 B1 | 7/2002 | Jones et al. |
| 6,425,395 B1 | 7/2002 | Brewer et al. |
| 6,427,689 B1 | 8/2002 | Estes et al. |
| 6,439,229 B1 | 8/2002 | Du et al. |
| 6,467,478 B1 | 10/2002 | Merrick et al. |
| 6,484,719 B1 | 11/2002 | Berthon-Jones |
| 6,512,938 B2 | 1/2003 | Claure et al. |
| 6,532,957 B2 | 3/2003 | Berthon-Jones |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,536,432 B2 | 3/2003 | Truschel |
| 6,539,940 B2 | 4/2003 | Zdrojkowski et al. |
| 6,543,449 B1 | 4/2003 | Woodring et al. |
| 6,546,930 B1 | 4/2003 | Emerson et al. |
| 6,550,478 B2 | 4/2003 | Remmers et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,561,187 B2 | 5/2003 | Schmidt et al. |
| 6,571,795 B2 | 6/2003 | Bourdon |
| 6,575,163 B1 | 6/2003 | Berthon-Jones |
| 6,578,575 B1 | 6/2003 | Jonson |
| 6,609,016 B1 | 8/2003 | Lynn |
| 6,609,517 B1 | 8/2003 | Estes et al. |
| 6,615,834 B2 | 9/2003 | Gradon et al. |
| 6,622,726 B1 | 9/2003 | Du |
| 6,626,175 B2 | 9/2003 | Jafari et al. |
| 6,629,527 B1 | 10/2003 | Estes et al. |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,644,316 B2 | 11/2003 | Bowman et al. |
| 6,659,101 B2 | 12/2003 | Berthon-Jones |
| 6,668,824 B1 | 12/2003 | Isaza et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,701,926 B2 | 3/2004 | Olsen et al. |
| 6,718,974 B1 | 4/2004 | Moberg |
| 6,722,365 B2 | 4/2004 | Nilsson et al. |
| 6,723,055 B2 | 4/2004 | Hoffman |
| 6,723,132 B2 | 4/2004 | Salehpoor |
| 6,725,447 B1 | 4/2004 | Gilman et al. |
| 6,739,337 B2 | 5/2004 | Isaza |
| 6,748,252 B2 | 6/2004 | Lynn et al. |
| 6,752,150 B1 | 6/2004 | Remmers et al. |
| 6,752,151 B2 | 6/2004 | Hill |
| 6,755,193 B2 | 6/2004 | Berthon-Jones et al. |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,789,541 B2 | 9/2004 | Olsen et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,837,242 B2 | 1/2005 | Younes |
| 6,843,250 B2 | 1/2005 | Efrati |
| 6,866,040 B1 | 3/2005 | Bourdon |
| 6,868,346 B2 | 3/2005 | Larson et al. |
| 6,874,503 B2 | 4/2005 | Rydgren |
| 6,910,480 B1 | 6/2005 | Berthon-Jones |
| 6,910,481 B2 | 6/2005 | Kimmel et al. |
| 6,920,875 B1 | 7/2005 | Hill et al. |
| 6,920,877 B2 | 7/2005 | Remmers et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 7,000,612 B2 | 2/2006 | Jafari et al. |
| 7,008,380 B1 | 3/2006 | Rees et al. |
| 7,013,892 B2 | 3/2006 | Estes et al. |
| 7,017,576 B2 | 3/2006 | Olsen et al. |
| 7,036,504 B2 | 5/2006 | Wallace et al. |
| 7,040,320 B2 | 5/2006 | Fjeld et al. |
| 7,055,522 B2 | 6/2006 | Berthon-Jones |
| 7,066,173 B2 | 6/2006 | Banner et al. |
| 7,073,501 B2 | 7/2006 | Remmers et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,092,757 B2 | 8/2006 | Larson et al. |
| 7,100,607 B2 | 9/2006 | Zdrojkowski et al. |
| 7,100,608 B2 | 9/2006 | Brewer et al. |
| 7,100,609 B2 | 9/2006 | Berthon-Jones et al. |
| 7,107,991 B2 | 9/2006 | Kolobow |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,168,429 B2 | 1/2007 | Matthews et al. |
| 7,195,028 B2 | 3/2007 | Basset et al. |
| 7,210,478 B2 | 5/2007 | Banner et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,331,343 B2 | 2/2008 | Schmidt et al. |
| 7,353,824 B1 | 4/2008 | Forsyth et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya et al. |
| 7,460,959 B2 | 12/2008 | Jafari |

(56) References Cited

U.S. PATENT DOCUMENTS

| | | |
|---|---|---|
| 7,475,685 B2 | 1/2009 | Dietz et al. |
| 7,487,773 B2 | 2/2009 | Li |
| 7,509,957 B2 | 3/2009 | Duquette et al. |
| 7,527,056 B2 | 5/2009 | Turiello |
| 7,533,671 B2 | 5/2009 | Gonzalez et al. |
| 7,621,269 B2 | 11/2009 | Turiello |
| 7,644,713 B2 | 1/2010 | Berthon-Jones |
| 7,654,802 B2 | 2/2010 | Crawford, Jr. et al. |
| 7,661,428 B2 | 2/2010 | Berthon-Jones |
| 7,673,629 B2 | 3/2010 | Turiello |
| 7,677,247 B2 | 3/2010 | Turiello |
| 7,694,677 B2 | 4/2010 | Tang |
| 7,694,678 B2 | 4/2010 | Turiello |
| 7,717,112 B2 | 5/2010 | Sun et al. |
| 7,717,113 B2 | 5/2010 | Andrieux |
| D618,356 S | 6/2010 | Ross |
| 7,770,578 B2 | 8/2010 | Estes et al. |
| 7,784,461 B2 | 8/2010 | Figueiredo et al. |
| 7,810,496 B2 | 10/2010 | Estes et al. |
| 7,810,497 B2 | 10/2010 | Pittman et al. |
| 7,814,906 B2 | 10/2010 | Moretti |
| 7,823,588 B2 | 11/2010 | Hansen |
| 7,827,988 B2 | 11/2010 | Matthews et al. |
| 7,855,716 B2 | 12/2010 | McCreary et al. |
| 7,856,979 B2 | 12/2010 | Doshi et al. |
| D632,796 S | 2/2011 | Ross et al. |
| D632,797 S | 2/2011 | Ross et al. |
| 7,882,835 B2 | 2/2011 | Eger et al. |
| 7,886,739 B2 | 2/2011 | Soliman et al. |
| 7,886,740 B2 | 2/2011 | Thomas et al. |
| 7,891,354 B2 | 2/2011 | Farbarik |
| 7,893,560 B2 | 2/2011 | Carter |
| 7,905,231 B2 | 3/2011 | Chalvignac |
| 7,918,222 B2 | 4/2011 | Chen |
| 7,918,223 B2 | 4/2011 | Soliman et al. |
| 7,920,067 B2 | 4/2011 | Durtschi et al. |
| 7,928,852 B2 | 4/2011 | Durtschi et al. |
| D638,852 S | 5/2011 | Skidmore et al. |
| 7,934,499 B2 | 5/2011 | Berthon-Jones |
| 7,938,114 B2 | 5/2011 | Matthews et al. |
| 7,963,283 B2 | 6/2011 | Sinderby |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,154 B2 | 8/2011 | Fontela et al. |
| D645,158 S | 9/2011 | Sanchez et al. |
| 8,021,309 B2 | 9/2011 | Zilberg |
| 8,021,310 B2 | 9/2011 | Sanborn et al. |
| 8,033,280 B2 | 10/2011 | Heinonen |
| D649,157 S | 11/2011 | Skidmore et al. |
| 8,051,853 B2 | 11/2011 | Berthon-Jones |
| 8,070,709 B2 | 12/2011 | Childers |
| 8,083,677 B2 | 12/2011 | Rohde |
| D652,521 S | 1/2012 | Ross et al. |
| D652,936 S | 1/2012 | Ross et al. |
| 8,105,310 B2 | 1/2012 | Klein |
| D653,749 S | 2/2012 | Winter et al. |
| 8,113,062 B2 | 2/2012 | Graboi et al. |
| 8,122,885 B2 | 2/2012 | Berthon-Jones et al. |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews et al. |
| 8,152,116 B2 | 4/2012 | Westberg |
| RE43,398 E | 5/2012 | Honkonen et al. |
| 8,181,643 B2 | 5/2012 | Friedberg |
| 8,181,648 B2 | 5/2012 | Perine et al. |
| 8,181,649 B2 | 5/2012 | Brunner |
| 8,187,184 B2 | 5/2012 | Muller et al. |
| 8,210,173 B2 | 7/2012 | Vandine |
| 8,210,174 B2 | 7/2012 | Farbarik |
| 8,211,128 B1 | 7/2012 | Facundus et al. |
| 8,216,159 B1 | 7/2012 | Leiboff |
| 8,217,218 B2 | 7/2012 | Court et al. |
| 8,225,796 B2 | 7/2012 | Davenport et al. |
| 8,235,930 B1 | 8/2012 | McCall |
| 8,240,684 B2 | 8/2012 | Ross et al. |
| 8,251,923 B2 | 8/2012 | Carrez et al. |
| 8,256,418 B2 | 9/2012 | Bassin |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,288,607 B2 | 10/2012 | Court et al. |
| 8,302,600 B2 | 11/2012 | Andrieux et al. |
| 8,302,602 B2 | 11/2012 | Andrieux et al. |
| 8,333,191 B2 | 12/2012 | Heinonen |
| 8,418,691 B2 | 4/2013 | Jafari et al. |
| 8,424,521 B2 | 4/2013 | Jafari et al. |
| 8,434,480 B2 | 5/2013 | Jafari et al. |
| 8,448,641 B2 | 5/2013 | Jafari et al. |
| 8,457,706 B2 | 6/2013 | Baker, Jr. |
| 8,459,260 B2 | 6/2013 | Bassin |
| D692,556 S | 10/2013 | Winter |
| D693,001 S | 11/2013 | Winter |
| D701,601 S | 3/2014 | Winter |
| 8,733,351 B2 | 5/2014 | Berthon-Jones |
| 8,789,526 B2 | 7/2014 | Kwok |
| 8,792,949 B2 | 7/2014 | Baker, Jr. |
| 8,910,633 B2 | 12/2014 | Younes |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 9,629,970 B2 | 4/2017 | Matthews |
| 9,675,771 B2 | 6/2017 | Jafari et al. |
| 10,207,068 B2 | 2/2019 | Jafari |
| 10,328,219 B2 | 6/2019 | Rao |
| 10,342,941 B2 | 7/2019 | Kwok |
| 10,350,379 B2 | 7/2019 | Sweeney |
| 2002/0014240 A1 | 2/2002 | Truschel |
| 2002/0053345 A1 | 5/2002 | Jafari et al. |
| 2002/0185126 A1 | 12/2002 | Krebs |
| 2003/0010339 A1 | 1/2003 | Banner et al. |
| 2003/0158466 A1 | 8/2003 | Lynn et al. |
| 2003/0159695 A1 | 8/2003 | Younes |
| 2003/0221689 A1 | 12/2003 | Berthon-Jones |
| 2004/0050387 A1 | 3/2004 | Younes |
| 2004/0074492 A1 | 4/2004 | Berthon-Jones |
| 2004/0089561 A1 | 5/2004 | Herman |
| 2004/0163648 A1 | 8/2004 | Burton |
| 2004/0187870 A1 | 9/2004 | Matthews et al. |
| 2005/0039748 A1 | 2/2005 | Andrieux |
| 2005/0109340 A1 | 5/2005 | Tehrani |
| 2005/0139212 A1 | 6/2005 | Bourdon |
| 2005/0172965 A1 | 8/2005 | Thulin |
| 2005/0188991 A1 | 9/2005 | Sun et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0086357 A1 | 4/2006 | Soliman et al. |
| 2006/0102180 A1 | 5/2006 | Berthon-Jones |
| 2006/0112959 A1 | 6/2006 | Mechlenburg et al. |
| 2006/0118112 A1 | 6/2006 | Cattano et al. |
| 2006/0144144 A1 | 7/2006 | Seto |
| 2006/0150974 A1 | 7/2006 | Berthon-Jones |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0174883 A1 | 8/2006 | Aylsworth et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0217633 A1 | 9/2006 | Glocker et al. |
| 2006/0235324 A1 | 10/2006 | Lynn |
| 2006/0241708 A1 | 10/2006 | Boute |
| 2006/0247508 A1 | 11/2006 | Fennell |
| 2006/0249150 A1 | 11/2006 | Dietz et al. |
| 2006/0249156 A1 | 11/2006 | Moretti |
| 2006/0254588 A1 | 11/2006 | Brewer et al. |
| 2006/0264762 A1 | 11/2006 | Starr |
| 2006/0272642 A1 | 12/2006 | Chalvignac |

(56) References Cited

U.S. PATENT DOCUMENTS

| | | |
|---|---|---|
| 2006/0278218 A1 | 12/2006 | Hoffman |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044796 A1 | 3/2007 | Zdrojkowski et al. |
| 2007/0068530 A1 | 3/2007 | Pacey |
| 2007/0072541 A1 | 3/2007 | Daniels, II et al. |
| 2007/0077200 A1 | 4/2007 | Baker |
| 2007/0089738 A1 | 4/2007 | Soliman et al. |
| 2007/0093721 A1 | 4/2007 | Lynn et al. |
| 2007/0101992 A1 | 5/2007 | Soliman et al. |
| 2007/0129647 A1 | 6/2007 | Lynn |
| 2007/0135736 A1 | 6/2007 | Addington et al. |
| 2007/0144522 A1 | 6/2007 | Eger et al. |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0221224 A1 | 9/2007 | Pittman et al. |
| 2007/0227537 A1 | 10/2007 | Bemister et al. |
| 2007/0251532 A1 | 11/2007 | Friedberg |
| 2007/0272241 A1 | 11/2007 | Sanborn et al. |
| 2007/0277823 A1 | 12/2007 | Al-Ali et al. |
| 2007/0283958 A1 | 12/2007 | Naghavi |
| 2007/0284361 A1 | 12/2007 | Nadjafizadeh et al. |
| 2008/0000478 A1 | 1/2008 | Matthiessen et al. |
| 2008/0000479 A1 | 1/2008 | Elaz et al. |
| 2008/0041382 A1 | 2/2008 | Matthews et al. |
| 2008/0041383 A1 | 2/2008 | Matthews et al. |
| 2008/0051674 A1 | 2/2008 | Davenport et al. |
| 2008/0053441 A1 | 3/2008 | Gottlib et al. |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0168988 A1 | 7/2008 | Lu |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0200775 A1 | 8/2008 | Lynn |
| 2008/0200819 A1 | 8/2008 | Lynn et al. |
| 2008/0221469 A1 | 9/2008 | Shevchuk |
| 2008/0251079 A1 | 10/2008 | Richey |
| 2008/0295837 A1 | 12/2008 | McCormick et al. |
| 2008/0302359 A1 | 12/2008 | Loomas et al. |
| 2009/0014007 A1 | 1/2009 | Brambilla et al. |
| 2009/0050153 A1 | 2/2009 | Brunner |
| 2009/0082653 A1 | 3/2009 | Rohde |
| 2009/0088613 A1 | 4/2009 | Marttila et al. |
| 2009/0093697 A1 | 4/2009 | Mir et al. |
| 2009/0137927 A1 | 5/2009 | Miller |
| 2009/0149730 A1 | 6/2009 | McCrary |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0178675 A1 | 7/2009 | Turiello |
| 2009/0178676 A1 | 7/2009 | Villax et al. |
| 2009/0194100 A1 | 8/2009 | Minagi |
| 2009/0205661 A1 | 8/2009 | Stephenson et al. |
| 2009/0205663 A1 | 8/2009 | Vandine et al. |
| 2009/0229605 A1 | 9/2009 | Efrati et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250061 A1 | 10/2009 | Marasigan |
| 2009/0272382 A1 | 11/2009 | Euliano et al. |
| 2009/0281481 A1 | 11/2009 | Harding |
| 2009/0301486 A1* | 12/2009 | Masic .................. A61B 5/08 128/204.21 |
| 2009/0301487 A1 | 12/2009 | Masic |
| 2009/0301490 A1 | 12/2009 | Masic |
| 2009/0301491 A1 | 12/2009 | Masic et al. |
| 2009/0308398 A1 | 12/2009 | Ferdinand et al. |
| 2009/0314294 A1 | 12/2009 | Chalvignac |
| 2009/0318851 A1 | 12/2009 | Schenck |
| 2010/0011307 A1 | 1/2010 | Desfossez et al. |
| 2010/0018529 A1 | 1/2010 | Chalvignac |
| 2010/0024819 A1 | 2/2010 | Tiedje |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078018 A1 | 4/2010 | Heinonen |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0081958 A1 | 4/2010 | She |
| 2010/0101574 A1 | 4/2010 | Bassin |
| 2010/0101576 A1 | 4/2010 | Berthon-Jones |
| 2010/0116276 A1 | 5/2010 | Bayasi |
| 2010/0137737 A1 | 6/2010 | Addington et al. |
| 2010/0139660 A1 | 6/2010 | Adahan |
| 2010/0147303 A1 | 6/2010 | Jafari et al. |
| 2010/0186741 A1 | 7/2010 | Aylsworth et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1* | 9/2010 | Jafari .................. A61M 16/026 128/204.23 |
| 2010/0234758 A1 | 9/2010 | de Menezes |
| 2010/0242961 A1 | 9/2010 | Mougel et al. |
| 2010/0249549 A1 | 9/2010 | Baker, Jr. et al. |
| 2010/0252048 A1 | 10/2010 | Young et al. |
| 2010/0258123 A1 | 10/2010 | Somaiya et al. |
| 2010/0262038 A1 | 10/2010 | Tan et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2010/0331768 A1 | 12/2010 | Hedmann et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0034863 A1 | 2/2011 | Hoffa |
| 2011/0041849 A1 | 2/2011 | Chen et al. |
| 2011/0041850 A1 | 2/2011 | Vandine et al. |
| 2011/0061648 A1 | 3/2011 | Durtschi et al. |
| 2011/0071367 A1 | 3/2011 | Court et al. |
| 2011/0077549 A1 | 3/2011 | Kitai et al. |
| 2011/0100373 A1 | 5/2011 | Efrati et al. |
| 2011/0125052 A1 | 5/2011 | Davenport et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |

(56) References Cited

U.S. PATENT DOCUMENTS

| | | |
|---|---|---|
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0178427 A1 | 7/2011 | Tan et al. |
| 2011/0196251 A1 | 8/2011 | Jourdain et al. |
| 2011/0201956 A1 | 8/2011 | Alferness et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0220112 A1 | 9/2011 | Connor |
| 2011/0226250 A1 | 9/2011 | LaBollita et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2011/0284003 A1 | 11/2011 | Douglas et al. |
| 2011/0290246 A1 | 12/2011 | Zachar |
| 2011/0293706 A1 | 12/2011 | Ludwig et al. |
| 2011/0313689 A1 | 12/2011 | Holley et al. |
| 2012/0000466 A1 | 1/2012 | Rapoport |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0006328 A1 | 1/2012 | Berthon-Jones |
| 2012/0022441 A1 | 1/2012 | Kelly et al. |
| 2012/0029317 A1 | 2/2012 | Doyle et al. |
| 2012/0030611 A1 | 2/2012 | Skidmore |
| 2012/0060835 A1 | 3/2012 | Mashak |
| 2012/0060841 A1 | 3/2012 | Crawford, Jr. et al. |
| 2012/0065533 A1 | 3/2012 | Carrillo, Jr. et al. |
| 2012/0071729 A1 | 3/2012 | Doyle et al. |
| 2012/0083729 A1 | 4/2012 | Childers |
| 2012/0090610 A1 | 4/2012 | O'Connor et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0139734 A1 | 6/2012 | Olde et al. |
| 2012/0150057 A1 | 6/2012 | Mantri |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0215081 A1 | 8/2012 | Euliano et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0123979 A1 | 5/2014 | Doyle et al. |
| 2014/0182590 A1 | 7/2014 | Platt et al. |
| 2014/0190485 A1 | 7/2014 | Milne |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090264 A1 | 4/2015 | Dong |
| 2017/0246409 A1 | 8/2017 | Jafari |

FOREIGN PATENT DOCUMENTS

| | | |
|---|---|---|
| EP | 1270036 | 1/2003 |
| WO | WO 94/23780 A | 10/1994 |
| WO | WO 98/06449 A | 2/1998 |
| WO | WO 00/10634 A | 3/2000 |
| WO | WO 00/45880 A | 8/2000 |
| WO | WO 01/74430 A | 10/2001 |
| WO | WO 02/28460 A | 4/2002 |
| WO | WO 03/055552 A1 | 7/2003 |
| WO | WO 04000114 | 12/2003 |
| WO | WO 2004/084980 A | 10/2004 |
| WO | WO 2005/105189 | 11/2005 |

(56) References Cited

FOREIGN PATENT DOCUMENTS

| WO | WO 2006/137784 A1 | 12/2006 |
| WO | WO 07145948 | 12/2007 |
| WO | WO 2009123981 | 10/2009 |

OTHER PUBLICATIONS

PCT International Search Report and Written Opinion in Application PCT/2009/038810, dated Jul. 6, 2009, 16 pgs.
PCT International Search Report and Written Opinion in Application PCT/2009/038815, dated Jul. 1, 2009, 14 pgs.
PCT International Search Report and Written Opinion in Application PCT/US09/038811, dated Jun. 7, 2009, 13 pgs.
PCT International Search Report and Written Opinion in Application PCT/US2009/038819, dated Jun. 26, 2009, 12 pgs.
PCT International Search Report and Written Opinion in Application PCT/US2009/038820, dated Jul. 22, 2009, 14 pgs.
PCT International Search Report and Written Opinion in Application PCT/US2009038818, dated Jul. 14, 2009, 15 pgs.
PCT International Search Report and Written Opinion in Application PCT/US201/0026618, dated Jun. 22, 2010, 19 pgs.
PCT International Search Report and Written Opinion in Application PCT/US2010/025485, dated Feb. 27, 2009, 8 pgs.
U.S. Appl. No. 12/238,248, Office Action dated Oct. 15, 2012, 12 pgs.
U.S. Appl. No. 12/238,248, Office Action dated May 14, 2012, 12 pgs.
U.S. Appl. No. 12/242,741, Notice of Allowance dated Jun. 5, 2012, 5 pgs.
U.S. Appl. No. 12/242,741, Office Action dated Jan. 10, 2012, 7 pgs.
U.S. Appl. No. 12/242,741, Supplemental Notice of Allowability dated Aug. 27, 2012, 2 pgs.
U.S. Appl. No. 12/242,756, Notice of Allowance dated Jun. 5, 2012, 5 pgs.
U.S. Appl. No. 12/242,756, Office Action dated Jan. 10, 2012, 7 pgs.
U.S. Appl. No. 12/242,756, Supplemental Notice of Allowability dated Aug. 27, 2012, 2 pgs.
U.S. Appl. No. 12/334,354, Notice of Allowance dated Jan. 27, 2012, 7 pgs.
U.S. Appl. No. 12/334,354, Notice of Allowance dated Oct. 5, 2012, 5 pgs.
U.S. Appl. No. 12/395,332, Office Action dated Sep. 13, 2012, 9 pgs.
U.S. Appl. No. 12/408,408, Notice of Allowance dated Jun. 4, 2012, 10 pgs.
U.S. Appl. No. 12/408,414, Amendment and Response filed Sep. 5, 2012, 7 pgs.
U.S. Appl. No. 12/408,414, Office Action dated Jun. 20, 2012, 9 pgs.
U.S. Appl. No. 12/414,419, Amendment and Response filed Aug. 27, 2012, 8 pgs.
U.S. Appl. No. 12/414,419, Notice of Allowance dated Sep. 19, 2012, 8 pgs.
U.S. Appl. No. 12/414,419, Office Action dated Jan. 20, 2012, 15 pgs.
U.S. Appl. No. 12/414,419, Office Action dated Jul. 18, 2012, 16 pgs.
U.S. Appl. No. 13/565,595, Notice of Allowance dated Nov. 2, 2012, 12 pgs.
U.S. Appl. No. 12/395,332, Notice of Allowance dated Dec. 24, 2012, 8 pgs.
U.S. Appl. No. 12/408,414, Notice of Allowance dated Dec. 10, 2012, 10 pgs.
U.S. Appl. No. 12/414,419, Notice of Allowance dated Jan. 8, 2013, 7 pgs.
U.S. Appl. No. 12/238,248, Advisory Action dated Jan. 4, 2013, 3 pgs.
U.S. Appl. No. 13/565,595, Notice of Allowance dated Feb. 25, 2013, 8 pgs.
Younes, M, et al., "Control of breathing relevant to mechanical ventilation", in Physiological Basis of Ventilatory Support, J.J. Marini and A.S. Slutsky, Ed., New York, Marcel Dekker, 1998, pp. 1-73.
Crooke, P.S. et al., "Patient-ventilator interaction: A general model for nonpassive mechanical ventilation", 1998, AMA Journal of Mathematics Applied in Medicine and Biology, 15, pp. 321-337.
U.S. Appl. No. 12/238,248, Office Action dated Apr. 26, 2013, 13 pgs.
840 Operator's and Technical Reference Manual. Ventilator System, Nellcor Puritan Bennett, Part No. 4-075609-00, Rev. G, Oct. 2006, pp. 1-424.
800 Operator's and Technical Reference Manual. Series Ventilator System, Nellcor Puritan Bennett, Part No. 4-070088-00, Rev. L, Aug. 2010, pp. 1-4 76.
7200 Ventilatory System: Addendum/Errata. Nellcor Puritan Bennett, Part No. 4-023576-00, Rev. A, Apr. 1998, pas. 1-32.
7200 Series Ventilator, Options, and Accessories: Operator's Manual. Nellcor Puritan Bennett, Part No. 22300 A, Sep. 1990, pp. 1-196.
Puritan Bennett 980 Series Ventilator Operator's Manual, Covidien, Jan. 29, 2014, Part. No. 10077893 A 2014-01, 506 pages.

* cited by examiner

METHODS AND SYSTEMS FOR LEAK ESTIMATION

CROSS-REFERENCE TO RELATED APPLICATIONS

This application is a continuation application of U.S. patent application Ser. No. 15/593,611, entitled "METHODS AND SYSTEMS FOR LEAK ESTIMATION," filed on May 12, 2017, which application is a continuation application of U.S. patent application Ser. No. 14/057,610 (now U.S. Pat. No. 9,675,771), filed on Oct. 18, 2013, the entire disclosures of which are hereby incorporated herein by reference.

Medical ventilator systems have long been used to provide ventilatory and supplemental oxygen support to patients. These ventilators typically comprise a source of pressurized gas which is fluidly connected to the patient through a conduit or tubing. Due to leaks and other factors, the volume of gas delivered by a ventilator system is not always the same volume of gas delivered to the lungs of the patient or exhaled by the patient. Leaks, if not accounted for, can impact triggering, cycling, and the adequacy of ventilation treatment.

Leak Estimation

This disclosure describes systems and methods for estimating internal leak flow. The term "leakage" or "leaks" refers to herein the air flow or volume that is input through the inspiratory module but that exits the patient tubing somewhere other than the expiratory valve. The internal leak or internal leak flow as used herein refers to any leak in the ventilation tubing system that occurs downstream of the proximal sensor (e.g., past the patient wye, such as in endotracheal tube cuff). The external leak or external leak flow as used herein refers to any leak in the ventilation tubing system that occurs prior to proximal sensor. The total leak or total leak flow refers to herein the air flow or volume that is input through the inspiratory module but that exits the patient tubing somewhere other than the expiratory valve and includes the internal leak and external leak. In part, the disclosure describes systems and methods for estimating internal leak flow, total leak flow, and/or external leak flow. In part, the disclosure describes systems and methods for displaying an estimated internal leak flow, estimated total leak flow, and/or estimated external leak flow. The disclosure further describes utilizing the internal leak flow, total leak flow, and/or external leak flow in other calculations, breath types, and for monitoring purposes. The disclosure also describes comparing the internal leak flow, total leak flow, and/or external leak flow and function thereof to a threshold to detect events, conditions, and/or improper ventilation. The disclosure further describes displaying recommended changes in ventilation or automatically changing ventilation based on the comparison of the internal leak flow, total leak flow, and/or external leak flow and functions thereof to a threshold.

In part, this disclosure describes a method for determining leakage during delivery of gas from a ventilator to a patient via a ventilation tubing system. The method includes:
  monitoring one or more measurements of at least one of pressure and flow by a proximal sensor; and
  estimating instantaneous internal leak flow of breathing gas inhaled or exhaled by the patient based on at least the one or more measurements by the proximal sensor.

The proximal sensor is located at a proximate (or proximal) location to the patient in a patient circuit or a patient interface Yet another aspect of this disclosure describes a ventilator system including a pressure generating system, a ventilation tubing system, sensors, and an internal leak module. The pressure generating system generates a flow of breathing gas. The ventilation tubing system includes a patient interface for connecting the pressure generating system to a patient. The sensors are operatively coupled to the ventilation tubing system. The sensors include a proximal sensor and at least one of an inspiratory sensor and an expiratory sensor. The sensors generate output indicative of at least one of flow and pressure. The internal leak module estimates an internal leak flow using at least sensor output from the proximal sensor.

The disclosure further describes a non-transitory computer-readable medium having computer-executable instructions executed by a processor of a controller. The controller includes an internal leak module and a total leak module. The internal leak module estimates internal leak flow based at least on sensor output from the proximal sensor. The total leak module estimates total leak flow based at least on sensor output from at least one of the inspiratory sensor and the expiratory sensor.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims.

DETAILED DESCRIPTION

Figure 1:
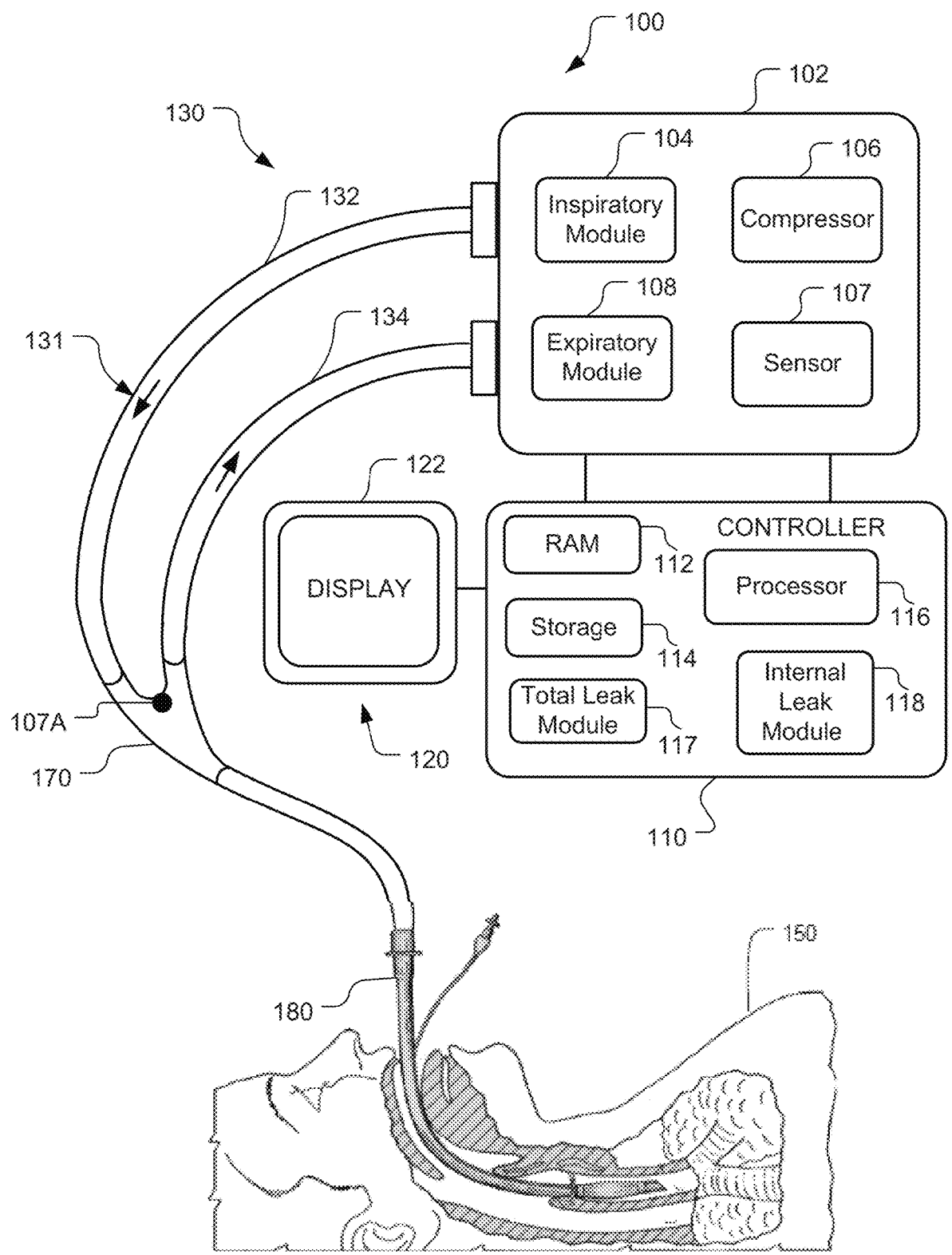
FIG. 1 illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

As each patient may require a different ventilation strategy, modern ventilators can be customized for the particular needs of an individual patient. For example, several different ventilator breath types have been created to provide better ventilation for patients in various different scenarios. In order execute these different breath types and treatments accurate monitored parameters are necessary. For example, while operating a ventilator, it is desirable to monitor the pressure, flow and/or volume of gas delivered to the patient and exhaled by the patient. Theses monitored parameters can be utilized for triggering, cycling, treatment monitoring, and etc. However, the patient interface and/or tubing system are prone to leaks, which if not accounted for impact the accuracy of breath delivery, patient-ventilator synchrony, and monitored data.

For example, leak management has a significant impact on ensuring proper functioning of the ventilator as well as the adequacy of the ventilation treatment and validity of reported patient data. Leak compensation is important during ventilation because treatment delivered through patient interfaces, such as masks and endotracheal tubes are prone to experience leaks. Accurate and timely detection, monitoring, and characterization of leak size under changing airway pressure conditions enhance treatment effectiveness, reduce a patient's work of breathing for triggering and cycling, and provide better advisory information for clinical decision making when compared to ventilation systems without leak compensation or poor leak compensation.

There are known leak detection and compensation product features available for medical ventilators. However, these conventional leak detection algorithms do not differentiate between internal leak (leaks occurring past the proximal sensor, e.g., from the endotracheal tube cuff, lung, etc.) and external leak (leaks occurring before the proximal sensor, e.g., patient circuit, inspiratory module connection etc.).

Accordingly, the current disclosure describes systems and methods for accurate leak estimation and/or compensation that account for total, internal, and/or external leaks during ventilation of a patient. The systems and method disclosed herein estimate the leak past the proximal sensor and proximal to the patient lungs. Various ventilator systems and methods described herein are provided with control schemes that provide improved leak estimation and/or compensation when compared to previous known leak estimation and/or compensation systems and methods that did not estimate an internal leak. Accordingly, the systems and methods disclosed herein provide accurate estimates of instantaneous internal leak rates and thus enhance patient monitoring and effectiveness under time-varying pressure conditions in the presence of both rigid orifice constant size leaks as well as pressure-dependent varying-size elastic leak sources.

FIG. 1 is a diagram illustrating an embodiment of an exemplary ventilator 100 connected to a human patient 150. As will be described in detail, the various ventilator system and method embodiments described herein may be provided with control schemes that provide improved leak estimation and/or compensation. These control schemes typically model leaks based upon factors, such as elastic properties and/or size variations of leak-susceptible components. However, these control schemes are suitable for modeling internal leak flow, which was not accounted for in prior ventilators. The present discussion will focus on specific example embodiments, though it should be appreciated that the present systems and methods are applicable to a wide variety of ventilator devices.

Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., mask) patient interface 180 and a patient circuit 131. Accordingly, the ventilation tubing system 130 includes the patient circuit 131, the proximal sensor 107A, the patient interface 180, and all connections to the pneumatic system 102 or components of the pneumatic system 102. The patient circuit 131 is the tubing that connects the pneumatic system 102 to the patient interface 180.

Leaks occur in a variety of settings, and the disclosure contemplates that the patient interface 180 may be invasive or non-invasive, and of any configuration suitable for communicating a flow of breathing gas from the patient circuit to an airway of the patient. Examples of suitable patient interface devices include a nasal mask, nasal/oral mask, nasal prong, full-face mask, tracheal tube, endotracheal tube, nasal pillow, etc.

The term "leakage" or "leaks" refers to herein the air flow or volume that is input through the inspiratory module but that exits the patient tubing somewhere other than the expiratory valve. The internal leak or internal leak flow as used herein refers to any leak in the ventilation tubing system that occurs downstream of the proximal sensor 107A. The external leak or external leak flow as used herein refers to any leak in the ventilation tubing system that occurs prior to proximal sensor 107A. The total leak or total leak flow refers to herein the air flow or volume that is input through the inspiratory module but that exits the patient tubing somewhere other than the expiratory valve and includes the internal leak and external leak.

The ventilation tubing system 130 may be a two-limb (shown) or a one-limb circuit for carrying gases to and from the patient 150. In a two-limb circuit embodiment, a fitting, typically referred to as a "wye" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. Specifically, inspiratory module 104 is associated with and/or controls one or more inspiratory valves for delivering gases to the patient 150 from a compressor 106 or another gas source. The expiratory module 108 is configured to release gases from the patient's lungs according to prescribed ventilatory settings. Specifically, expiratory module 108 is associated with and/or controls one or more expiratory valves for releasing gases from the patient 150. In some embodiments, pneumatic system 102, inspiratory module 104 and/or expiratory module 108 is/are configured to provide ventilation according to various breath types.

The ventilator 100 may also include one or more sensors 107 communicatively coupled to ventilator 100. The sensors 107 may be located in the pneumatic system 102, ventilation tubing system 130 (such as the wye 170), and/or on the patient 150. The embodiment of FIG. 1 illustrates a sensor 107 in pneumatic system 102 and at the wye of the ventilation tubing system 130.

Sensors 107 may communicate with various components of ventilator 100, e.g., pneumatic system 102, other sensors 107, processor 116, controller 110, total leak module 117, internal leak module 118, and any other suitable components and/or modules. In one embodiment, sensors 107 generate output and send this output to pneumatic system 102, other sensors 107, processor 116, controller 110, total leak module 117, internal leak module 118, and any other suitable components and/or modules. Sensors 107 may employ any suitable sensory or derivative technique for monitoring one or more patient parameters or ventilator parameters associated with the ventilation of a patient 150.

As used herein, patient parameters are any parameters determined based on measurements taken of the patient 150, such as heart rate, respiration rate, a blood oxygen level (SpO$_2$), inspiratory lung flow, airway pressure, and etc. As used herein, ventilator parameters are parameters that are determined by the ventilator 100 and/or are input into the ventilator 100 by an operator, such as a breath type, desired patient effort, support setting, and etc. Some parameters may be either ventilator and/or patient parameters.

Sensors 107 may detect changes in patient parameters. For example, sensor(s) 107 may include a flow sensor and/or a pressure senor. These sensors 107 generate output showing the flow and/or the pressure of breathing gas delivered to the patient 150, exhaled by the patient 150, at the circuit wye, delivered by the ventilator 100, and/or within the ventilation tubing system 130. In some embodiments, a differential pressure transducer or sensor is utilized to calculate flow. Accordingly, a flow sensor as used herein includes a pressure sensor and a pressure sensor as used herein includes a flow sensor. In some embodiments, net volume, tidal volume, inspiratory volume, proximate volume, and/or an expiratory volume are determined based on the senor output from the flow sensor and/or pressure sensor.

Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in a proximate location to the patient 150 in the ventilation tubing system 130, such as in or near a wye 170 and/or a patient interface 180. Any sensor 107 located in the proximate location is referred to herein as a proximal sensor. In some embodiments, the proximate location is within 1 foot, 6 inches, or 1 inch of the patient 150. In alternative embodiments, the proximate location is within the patient 150, such as a location located within an endotracheal tube inserted in the trachea of the patient. Indeed, any sensory device useful for monitoring changes in measurable parameters during ventilatory treatment may be employed in accordance with embodiments described herein.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated/calculated using a model, such as a model derived from the Equation of Motion (e.g., Target Airway Pressure(t)=$E_p \int Q_p dt + Q_p R_p$ – Patient Effort(t)). $E_p$ is equal to respiratory elastance (inverse of respiratory compliance). $R_p$ is the respiratory resistance. $Q_p$ is the patient flow (inspiratory or expiratory). t is the time. Leak-compensated patient flow (leak compensated $Q_p$) enables more accurate determination of respiratory parameters and breath delivery by ventilators.

The pneumatic system 102 may include a variety of other components, including mixing modules, valves, tubing, accumulators, filters, etc. Controller 110 is operatively coupled with pneumatic system 102, signal measurement and acquisition systems, sensor 107, display 122, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. Display 122 may also provide useful information in the form of various ventilatory data regarding the physical condition of a patient 150. The useful information may be derived by the ventilator 100, based on data collected by a processor 116 or controller 110, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system or display coupled via any suitable way to the ventilator 100.

In some embodiments, the display 122 displays total leak flow, averaged total leak flow, internal leak flow, averaged internal leak flow, external leak flow, and/or averaged external leak flow. In further embodiments, the display 122 displays a graph, chart or list of total leak flow, averaged total leak flow, internal leak flow, averaged internal leak flow, external leak flow, and/or averaged external leak flow for a predetermined number of computational cycle(s), a predetermined amount of time, or predetermined number of breaths. In yet further embodiments, the display 122 displays event detection or ventilation treatment options based on the comparison of the internal leak flow and/or the total leak flow to predetermined thresholds. For example, the display 122 may display a tube or patient circuit disconnect notice based on a comparison of a ratio of total leak flow to internal leak flow to a disconnect threshold.

Controller 110 may include memory 112, one or more processors 116, storage 114, and/or other components of the type commonly found in command and control computing devices. Controller 110 may further include a total leak module 117 and/or an internal leak module 118 as illustrated in FIG. 1. The controller 110 is configured to deliver gases to the patient 150 according to prescribed or selected breath types and/or modes of ventilation. In alternative embodiments, the total leak module 117 and/or the internal leak module 118 may be located in other components of the ventilator 100, such as the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

In some embodiments, the total leak module 117, the effort module 115, the internal leak module 118, and/or the trigger module 113 are part of the controller 110 as illustrated in FIG. 1. In other embodiments, the total leak module 117, the effort module 115, the internal leak module 118, and/or the trigger module 113 may are part of the processor 116, pneumatic system 102, and/or a separate computing device in communication with the ventilator 100.

Errors may be introduced due to leaks in the ventilation tubing system 130. The term ventilation tubing system 130 is used herein to describe the patient circuit 131, any equipment attached to or used in the ventilation tubing system 130 such as water traps, monitors, drug delivery devices, etc. (not shown), and the patient interface 180. Depending on the embodiment, this may include some equipment contained in the inspiratory module 104 and/or the expiratory module 108.

Accordingly, the controller 110 of the ventilator 100 includes a total leak module 117. The total leak module 117 of the ventilator 100 determines or estimates the total leak flow of the ventilation tubing system 130. When referring to total leak in or from the ventilation tubing system 130, such leaks include leaks within the ventilation tubing system 130 and leaks where the ventilation tubing system 130 connects to the pressure generator 102 or the patient 150. Thus, leaks from the ventilation tubing system 130 (i.e., total leak) include leaks from the patient circuit 131, leaks from the patient interface 180 (e.g., masks are often provided with holes or other pressure relief devices through which some leakage may occur), leaks from the point of connection of the patient interface 180 to the patient 150 (e.g., leaks around the edges of a mask due to a poor fit or patient movement), and leaks from the point of connection of the patient interface 180 to the patient circuit 131 (e.g., due to a poor connection between the patient interface 180 and the circuit 131). In further embodiments, the leaks also account for leaks occurring within the patient 150, such as an endotracheal tube within the patient that has become dislodged from the patient's esophagus or lungs. The total leak flow includes an internal leak flow and an external leak flow of the ventilation tubing system 130.

While a variety of leak estimation and leak calculation techniques may be used by the total leak module 117, in some embodiments leak calculation is performed in a manner similar to that described in U.S. Provisional Application 61/041,070, previously incorporated herein by reference. Improved leak estimation may be achieved in the present examples through provision of a modeling scheme that more fully accounts for factors affecting the time-varying magnitude of leaks under interface and airway pressure variations. It has been determined that not accounting for elastic leakage from the ventilation tubing system 130 can cause many problems. First, if only the inelastic/fixed orifice model is used to estimate leak, the subsequent errors caused by ignoring the elastic effects of any actual leaks end up generating inaccurate estimates of flow rates into the lung. Second, if the elasticity of the leak source is ignored, any other calculation, estimate, or action that the ventilator 100 may perform which is affected by the leak estimate will be less accurate. Accordingly, in some embodiments, the total leak module 117 and/or the internal leak module 118 determines or estimates the instantaneous total leak by accounting for both fixed (rigid) and elastic components of the system leakage. In some of these embodiments, the total leak module 117 utilizes in part, a constant-size leak model consisting of a single parameter (orifice resistance, leak conductance, or leak factor) utilized in conjunction with the pneumatic flow equation through a rigid orifice, namely:

$$Q_{leak} = (\text{leak factor/Resistance/Conductance}) * \sqrt{\Delta P} \qquad \text{EQ \#1}$$

where $\Delta P$=pressure differential across the leak site. This assumes a fixed size leak (i.e., a constant leak resistance or conductance or factor over at least one breath period).

To provide a more accurate estimate of instantaneous leak, the total leak module 117 also takes into account the elastic properties of one or more components of the ventilator device (e.g., the face mask, tubing used in the patient circuit, etc.). This more accurate leak accounting enhances patient-ventilator synchrony and effectiveness under time-varying airway pressure conditions in the presence of both rigid orifice constant size leaks as well as pressure-dependent varying-size elastic leak sources.

According to the pneumatic equations governing the flow across an orifice, the flow rate is a function of the area of the orifice and the square root of the pressure difference across the orifice as well as gas properties. For derivation of the algorithm carried out by the total leak module 117, constant gas properties are assumed and a combination of leak sources comprising of rigid fixed-size orifices (total area=$A_r$=constant) and elastic opening through the patient interface [total area =$A_e$(P)=function of applied pressure].

Therefore, $$Q_{leak}=K_0*(A_r+A_e(P))*\sqrt{\Delta P} \quad \text{EQ \#2}$$

where $K_0$=assumed constant.

For the purposes of this implementation, at low pressure differences, the maximum center deflection for elastic membranes and thin plates are a quasi-linear function of applied pressure as well as dependent on other factors such as radius, thickness, stress, Young's Modulus of Elasticity, Poisson's Ratio, etc. Therefore, $$A_e(P)=K_e*\Delta P \quad \text{EQ \#3}$$

where $K_e$=assumed constant. As $\Delta P$ is the pressure difference across a leak source to ambient ($P_{ambient}=0$), then we substitute $\Delta P$ by the instantaneous applied pressure P(t) and rearrange EQ #1 as follows ($K_1$ and $K_2$ are assumed to be constant):

$$Q_{leak}=K_0(A_r+K_e*P(t))\sqrt{\Delta P} \quad \text{EQ \#4}$$

$$Q_{leak}=K_1*P(t)^{1/2}+K_2*P(t)^{3/2} \quad \text{EQ \#5}$$

Also, the total volume loss over one breath period=$V_{leak}$=Delivered Volume−Exhausted Volume:

$$V_{leak} = \int_0^{Tb}\left[K_1 P(t)^{\frac{1}{2}} + K_2 P(t)^{\frac{3}{2}}\right] dt \quad \text{EQ \#6}$$

$$\int_0^{Tb} [Q_{delivered} - Q_{exh}] * dt$$

where Tb=full breath period.

The general equation of motion for a patient ventilator system can be written as follows:

$$P_{aw}+P_m=R*(Q_{leak}+Q_{exh}-Q_{delivered})+(1/C)*\int[Q_{leak}+Q_{exh}-Q_{delivered}]*dt \quad \text{EQ \#7}$$

where $P_{aw}$=airway pressure, $P_m$=muscle pressure (or patient effort), R=resistance, and C=compliance.

During passive exhalation, assuming that when end exhalation conditions are present a constant airway pressure is being delivered (steady positive-end-expiratory pressure (PEEP)), constant bias flow maintained during exhalation phase $Q_{delivered}$, constant leak flow (due to no pressure variation), and $P_m$=0 (due to no patient respiratory effort), the equation of motion could be differentiated and reorganized as follows:

$$\frac{dP_{aw}}{dt} = 0 = R*Q_{exh}\text{dot} + \frac{Q_{leak}+Q_{exh}-Q_{delivered}}{C} \quad \text{EQ \#8}$$

$$Q_{leak} = (Q_{delivered}-Q_{exh}) - R*C*Q_{exh}\text{dot} \quad \text{EQ \#9}$$

where $Q_{exh}$dot=time derivative of exhausted flow. If $Q_{exh}$dot=0 (i.e., $Q_{exh}$ is constant, no variation in time), then EQ #8 can be reduced to the following equation:

$$Q_{leak}=Q_{delivered}-Q_{exh} \quad \text{EQ \#10}$$

And subsequently, $$Q_{leak}K_1*(PEEP)^{1/2}+K_2*(PEEP)^{3/2} \quad \text{EQ \#11}$$

Otherwise, $Q_{exh}$dot≠0 ($Q_{exh}$ is not constant, there is variation with time). In this case, an appropriate duration of time $\Delta T$ is taken during passive exhalation period and assuming constant delivered flow, an equation can be derived as follows:

$$R*C = \frac{(Q_{exh}(t)+\Delta T)-Q_{exh}(t)}{(Q_{exh}\text{dot}(t)+\Delta T)-Q_{exh}dot(t)} \quad \text{EQ \#12}$$

and, $$Q_{leak}(t_i+\Delta T) = \quad \text{EQ \#13}$$
$$K_1(PEEP)^{\frac{1}{2}} + K_2(PEEP)^{\frac{3}{2}} = [Q_{delivered}(t_i+\Delta T) -$$
$$Q_{exh}(t_i+\Delta T)] - R*C*Q_{exh}\text{dot}(t_i+\Delta T)$$

Therefore, EQ #6 and EQ #10 (when $Q_{exh}$dot=0) or EQ #6 and EQ #13 (when $Q_{exh}$dot≠0) may be used by the total leak module 117 to solve for $K_1$ and $K_2$. These calculations may be repeated by the total leak module 117 periodically, such as every breath cycle or computational cycle, and applied over appropriate time windows (i.e. during exhalation) and breathing conditions to optimize parameter estimation and minimize the total error between estimated total volume loss and actual measured volume loss across the full breath cycle. In further embodiments, the total leak module 117 stores and/or compares the constants $K_1$ and $K_2$ to track changes and update various parameters of the system such as the triggering and cycling sensitivities, etc.

In additional embodiments, the total leak module 117 calculates the averaged total leak flow for a predetermined number of breaths, for a predetermined number of computational cycles, or for a predetermined amount of time.

The total leak module 117 communicates with other components of the ventilator 100. In some embodiments, the total leak module 117 communicates with the sensors 107, pneumatic system 102, display module 120, internal leak module 118, processor 116, and/or controller 110. For example, the total leak module 117 can send the total leak flow to the display module 120 for displaying the total leak flow. In alternative embodiments, any other suitable component of the ventilator may perform the functions of the total leak module 117, such as the pneumatic system 102, internal leak module 118, processor 116, and/or controller 110.

In alternative embodiments, other components of the ventilator 100, such as the pneumatic system 102, controller 110, and internal leak module 118 may be utilized to perform the functions of the total leak module 117. This list is exemplary only and is not meant to be limiting. Any suitable component of the ventilator 100 may be utilized to determine the total leak flow.

As discussed above, systems and method for determining total leak flow were previously available for ventilators. However, these conventional leak detection algorithms do not differentiate between internal leak flow and total leak flow. Additionally, these conventional leak detection algorithms do not differentiate between internal leak flow and external leak flow. As discussed above, the more accurate the leak estimation, the better the baseline calculation of delivered and exhaled volume, patient effort, resistance, and compliance as well as event detection (triggering and cycling phase transitions). Further, knowing the total leak flow and what portion of the total leak flow is an internal leak flow provides the clinician with additional useful information for effective ventilation treatment and event detection. For example, if a large percentage of the total leak flow is the internal leak flow, the operator knows that a significant amount of the leak is occurring in or near the patient interface or within the patient. For example, the information may be used to evaluate the integrity of the placement of the endotracheal tube. In an alternative example, if a very small percentage of the total leak flow is the internal leak flow, the operator knows that a significant amount of the leak is occurring in the patient circuit or at ventilator connections to the patient circuit.

Accordingly, the controller 110 of the ventilator 100 further includes an internal leak module 118. The internal leak module 118 determines or estimates the internal leak flow of the ventilation tubing system 130. When referring to the internal leak flow in or from the ventilation tubing system 130, such leaks include any leaks within the ventilation tubing system 130 downstream (that is on the patient side) of the proximal sensor 107A and leaks where the ventilation tubing system 130 connects to the patient 150. Accordingly, the internal leak flow includes leaks in the patient circuit 131 downstream from the proximal sensor 107A, leaks from the patient interface 180 (if the proximal sensor is located upstream the interface), leaks from the point of connection of the patient interface 180 to the patient 150, and leaks from the point of connection of the patient interface 180 to the patient circuit 131 (if the proximal sensor is located upstream). In further embodiments, the internal leak flow also accounts for leaks occurring within the patient 150, such as an endotracheal tube within the patient that has become dislodged from the patient's esophagus or lungs.

The internal leak module 118 determines or estimates the instantaneous internal leak flow by accounting for both fixed (rigid) and elastic components of the system leakage. Accordingly, the internal leak module 118, similarly to the total leak module 117, assumes constant gas properties and a combination of leak sources comprising of rigid fixed-size orifices (total area=$A_r$=constant) and elastic openings proximal to the patient [total area=$A_e(P)$=changing as a function of applied pressure]. However, unlike the total leak module 117, the internal leak module 118 utilizes sensor output from a proximal sensor, such as proximal flow and/or pressure sensor. In some embodiments, the proximal sensor is located at the wye 170 of the patient circuit 131. Additionally, unlike the total leak module 117, the internal leak module 118 estimates the lung pressure across the patient interface 180, such as the endotracheal tube, using an appropriate model, such as the Rohrer equation, shown below:

$$\text{Interface Pressure Drop} = h_1 * Q + h_2 * Q^r \qquad \text{EQ \#14}$$

where r=power exponent for flow rate (e.g., typical values assumed to be equal to 1.75-2.00) and $h_1$ and $h_2$ are derived empirically for each patient interface size by characterizing the pressure drop for various flow rates using nonlinear regression analysis to determine the best fit.

Estimated Lung Pressure (Inhalation)=$P_{inh}$ $P_{inh}$=(Proximate Pressure Sensor Output)−(Interface Pressure Drop);

Estimated Lung Pressure (Exhalation)=$P_{exh}$ $P_{exh}$=(Proximate Pressure Sensor Output)+(Interface Pressure Drop); and $P(t)=P_{inh}$ or $P_{exh}$ depending upon the breath phase (direction of the flow into or out of the lung). Thus, $$Q_{leak_y} = K_0 * (A_r + A_e(P)) * \sqrt{\Delta P_y} \qquad \text{EQ \#15}$$

where $K_0$=assumed constant, $Q_{leak_y}$=estimated internal leak flow rate.

For the purposes of this implementation, at low pressure differences, the maximum center deflection for elastic membranes and thin plates are a quasi-linear function of applied pressure as well as dependent on other factors such as radius, thickness, stress, Young's Modulus of Elasticity, Poisson's Ratio, etc. Therefore, $$A_e(P) = K_e * \Delta P_y \qquad \text{EQ \#16}$$

where $K_e$=assumed constant. The $\Delta P_y$ is the pressure difference across an internal leak source to ambient ($P_{ambient}$). $P_{ambient}$ is the pressure outside the leak source, for example outside the endotracheal tube cuff. For simplicity of derivation and approximation, it is assumed that $P_{ambient}=0$. If $P_{ambient}=0$, then $\Delta P_y$ is substituted by the instantaneous applied pressure $P(t)$ and EQ #15 can be rearranged as follows ($K_{y1}$ and $K_{y2}$ are assumed to be constant):

$$Q_{leak_y} = K_0 * (A_r + K_e * P(t)) \sqrt{\Delta P_y}; \qquad \text{EQ \#17}$$

$$Q_{leak_y} = K_{y1} * P(t)^{1/2} + K_{y2} * P(t)^{3/2} \qquad \text{EQ \#18}$$

Also, the total volume loss over one breath period=$V_{leak_y}$=Delivered volume based on the proximal sensor output−Exhausted volume based on the proximate sensor output:

$$V_{leak_y} = \int_0^{Tb} [K_{y1} P(t)^{1/2} + K_{y2} P(t)^{3/2}] dt \qquad \text{EQ \#19}$$

$$\int_0^{Tb} [Q_{lung} - Q_{exh}] * dt$$

where Tb=full breath period, $Q_{lung}$=flow going into the lung, and $P(t)=P_y$. However, unlike the total leak module 117, the internal leak module 118 utilizes flow and pressure measurements based on the output from proximal sensor. When the proximal sensor flow readings are bidirectional (change sign based on respiration phase) equation 19 may be rewritten as follows:

$$V_{leak_y} = \int_0^{Tb} [K_{y1} P(t)^{1/2} + K_{y2} P(t)^{3/2}] dt$$

$$\int_0^{Tb} [Q_{prox}] * dt$$

When $V_{leak_y} \neq 0$, i.e., in presence of internal leak which makes the leak-compensating flow to move through the proximal sensor towards the lung, the general equation of motion for a patient ventilator system during passive exhalation can then be written as follows:

$$P_{lung} = (1/C) * \int [Q_{prox} - Q_{leak_y}] * dt \qquad \text{EQ \#20}$$

where $P_{lung}$ is estimated lung pressure, C is compliance, and $Q_{prox}$ total flow into the patient is where P interface as monitored by the proximal sensor.

Assuming end exhalation conditions to imply steady PEEP (i.e., constant airway pressure), constant bias flow (delivered by the ventilator) providing sufficient flow to compensate for the internal leak flow and maintain PEEP by regulating the exhalation valve, constant leak size, and no patient respiratory effort, the equation can be differentiated and derive:

$$\frac{dP_{lung}}{dt} = 0 = \frac{Q_{prox} - Q_{leak_y}}{C}; \text{ where } Q_{leak_y} = Q_{prox}. \qquad \text{EQ \#21}$$

-continued where                                                                  EQ #21

$Q_{leak_y} = Q_{prox}$;

$\frac{dP_{lung}}{dt}$ = rate of change of $P_{lung}$ over time

So if $Q_{exh}$Prox=constant (rate of change of Qprox during exhalation is zero), we will have:

$$Q_{leak_y} = Q_{prox} \qquad \text{EQ \#22}$$

The flow measurements from the proximate sensor provided at every sample time are a single measurement regardless of whether the breath is in exhalation or inhalation. The only difference is that the sign (positive or negative) of the measurement will change (i.e., sensor flow readings are bidirectional). The flow measurements by the proximate sensor are negative (i.e., $Q_{exh}$prox) during exhalation. The flow measurements by the proximate sensor are positive (i.e., $Q_{inh}$prox) during inhalation. However, for calculation of pressure drop across the endotracheal tube, the ventilator uses the absolute magnitude of the proximal flow reading and uses the calculated pressure drop in accordance to the flow direction (or breath phase). During inhalation, the flow is going into the lung and $P_{lung}$=Pprox−interface pressure drop; on the other hand during exhalation, the flow is going out of the lung and $P_{lung}$=Pprox+interface pressure drop. In the presence of internal leaks, the leak-compensating flow during exhalation will be moving into the lung and thus will be reported positive and $P_{lung}$=Pprox−interface pressure drop. Subsequently, $$Q_{leak_y} = K_{y1}*(PEEP-h_1*Q_{prox}-h_2*Q_{prox}^r)^{1/2} + K_{y2}*(PEEP-h_1*Q_{prox}-h_2*Q_{prox}^r)^{3/2} \qquad \text{EQ \#23}$$

Otherwise, $Q_{exh}$Prox or $P_{lungExh}$≠constant ($P_{lung}$ varies over time during exhalation), taking an appropriate time window (ΔT) during passive exhalation period and assuming constant delivered flow, we could derive:

$$Q_{Leak_y}(t_i+\Delta T) = K_{y1}*(PEEP-h_1*Q_{prox}-h_2*Q_{prox}^r)^{1/2} + K_{y2}*(PEEP-h_1*Q_{prox}-h_2*Q_{prox}^r)^{3/2} = [Q_{exh}prox(t_i+\Delta T)] \qquad \text{EQ \#24}$$

where $h_1$, $h_2$, and r are Rohrer model characterization parameters for the interface pressure drop. Therefore, equations 19 and 22 ($Q_{exh}$Prox when $P_{lungExh}$=constant) or 19 and 24 ($Q_{exh}$Prox when $P_{lungExh}$≠constant) may be used to solve for $K_{y1}$ and $K_{y2}$. These calculations may be repeated by the internal leak module 118 periodically, such as every breath cycle or computational cycle, and applied over appropriate time windows (i.e. during exhalation) and breathing conditions to optimize parameter estimation and minimize the total error between estimated total volume loss and actual measured volume loss across the full breath cycle. In further embodiments, the internal leak module 118 stores and/or compares the constants $K_{y1}$ and $K_{y2}$ to track changes and update various parameters of the system.

In additional embodiments, the internal leak module 118 calculates the averaged internal leak flow for a predetermined number of breaths or computational cycles.

The internal leak module 118 communicates with other components of the ventilator 100. In some embodiments, the internal leak module 118 communicates with the sensors 107, pneumatic system 102, display module 120, total leak module 117, processor 116, and/or controller 110. For example, the internal leak module 118 can send the internal leak flow to the display module 120 for displaying the internal leak flow.

In alternative embodiments, any other suitable component of the ventilator may perform the functions of the internal leak module 118, such as the pneumatic system 102, total leak module 117, processor 116, and/or controller 110. This list is exemplary only and is not meant to be limiting. Any suitable component of the ventilator 100 may be utilized to determine the internal leak flow.

In some embodiments, the internal leak module 118 of the ventilator 100 determines the external leak flow based on the total leak flow and the internal leak flow. In alternative embodiments, the total leak module 117 of the ventilator 100 determines the external leak flow based on the total leak flow and the internal leak flow. In some embodiments, the external leak flow is determined by subtracting the internal leak flow from the external leak flow. In other embodiments, the total leak flow and the internal leak flow are adjusted to account for the errors and signal delays of each of the different sensors and ventilator components utilized to determine the internal leak flow and total leak flow. The component of the ventilator 100 calculating/estimating the external leak flow may communicate with other ventilator components, such as the internal leak module 118, the pneumatic system 102, total leak module 117, processor 116, sensor 107, display module 120, and/or controller 110. For example, the internal leak module 118 or the total leak module 117 of the ventilator 100 calculating/estimating the external leak flow can send the external leak flow to the display module 120 for displaying the external leak flow.

In additional embodiments, the internal leak module 118 and/or the total leak module 117 tracks and graphs the averaged internal leak flow, the averaged total leak flow, internal leak flow, the total leak flow, the averaged external leak flow, and/or the external leak flow for a predetermined number of breaths, number of computational cycles, or amount of time. In other embodiments, the display module 120 or the controller 110 tracks and graphs the averaged internal leak flow, the averaged total leak flow, internal leak flow, the total leak flow, the averaged external leak flow, and/or the external leak flow for a predetermined number of breaths, number of computational cycles, or amount of time.

The controller 110 or any other suitable component of the ventilator 100 may utilize the total leak flow and/or the internal leak flow to estimates a leak compensated lung flow. The leak compensated lung flow may be utilized in other ventilator calculations and modes to improve accuracy and synchrony of other ventilator calculations, breath types, and modes, such as triggering, estimation of resistance, estimation of compliance, estimation of patient effort (or muscle pressure), proportional assist breath type, volume-targeted-pressure controlled breath type, and etc.

In some embodiments, the ventilator utilizes the internal leak flow or the internal leak flow and the total leak flow for event detection or ventilator treatment. In further embodiments, a detected event may be communicated to the display module 120 to display a notification or warning of the detected event. For example, the controller 110 or any other suitable component of the ventilator 100 may compare the ratio of internal leak flow to total leak flow to a disconnect threshold to determine if the patient circuit (i.e., endotracheal tube) is disconnected. For example, if the controller determines that the internal leak flow is 90%, 95%, 99%, 99.5% or more of the total leak flow, the controller determines a possible patient interface disconnection and sends instructions to the display module 120 to display the notice of possible patient interface disconnection. In an alternative example, if the controller determines that the internal leak flow is 90%, 95%, 99%, 99.5% or more of the total leak and the total leak flow is high (i.e., above some predetermined disconnection threshold), the controller determines a possible patient interface disconnection and sends instructions to the display module 120 to display the notice of possible patient interface disconnection. Based on these instructions, the display module 120 would display a patient interface disconnection notice or warning.

Figure 2:
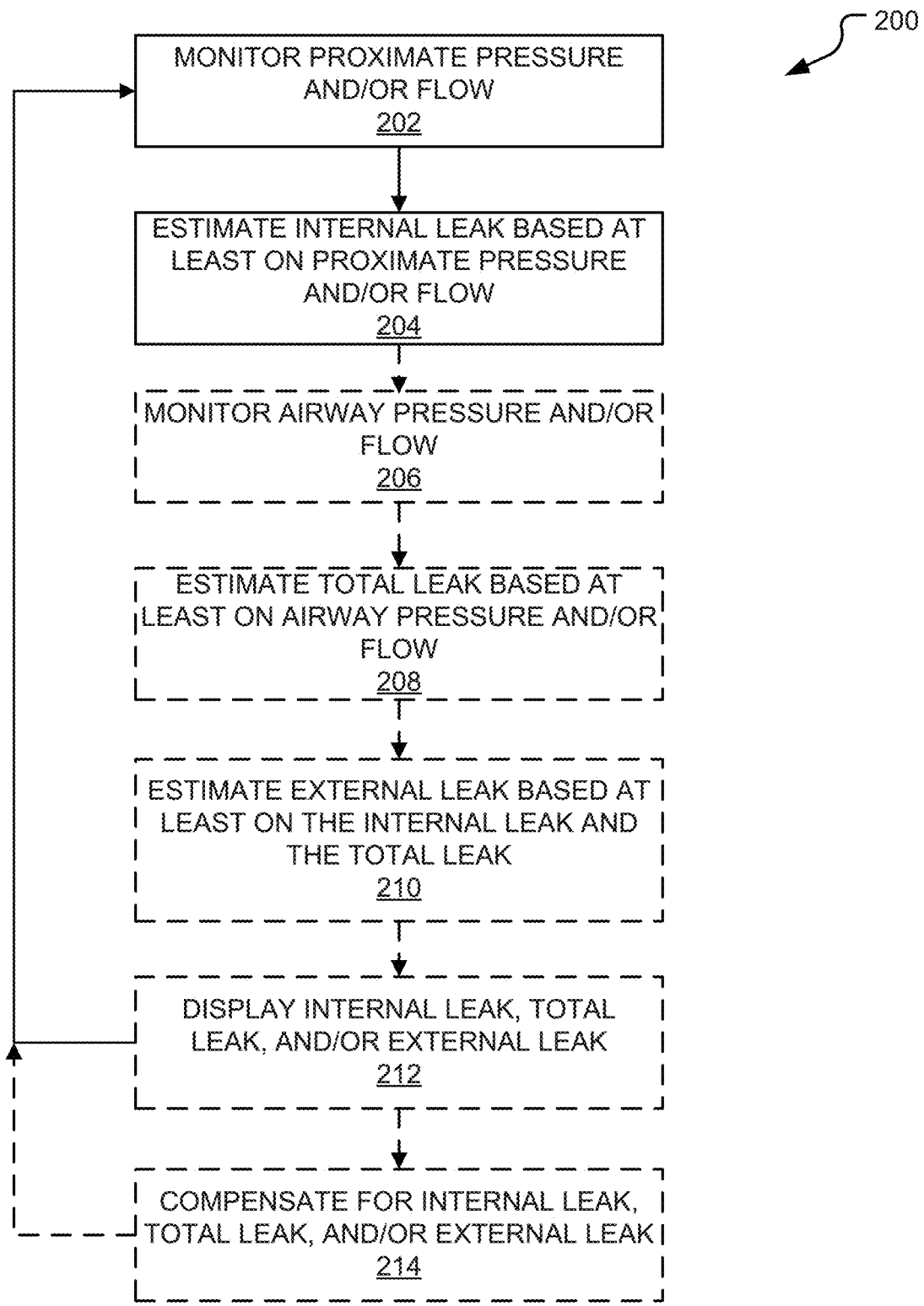
FIG. 2 illustrates an embodiment of a method for determining leakage during ventilation.

FIG. 2 illustrates a method 200 for determining leakage during delivery of gas from a ventilator to a patient via a ventilation tubing system. During ventilation, breathing gas is delivered to a patient from a gas source via the ventilation tubing system. Due to leaks and other factors, the volume of gas delivered by a ventilator system is not always the same volume of gas delivered to the lungs of the patient or exhaled by the patient. Leaks, if not accounted for, can impact triggering, cycling, and the adequacy of ventilation treatment. There are known leak detection and compensation product features available for medical ventilators. However, these conventional leak flow detection algorithms do not differentiate between internal leak flow (leaks occurring past the proximal sensor, e.g., in the endotracheal tube cuff, lung, etc.) and external leak flow (leaks occurring before the proximal sensor, e.g., in the patient circuit, etc.). Accordingly, method 200 determines the internal leak flow. The method 200 may be performed automatically when the ventilator is ventilating a patient or may only be active during specific times, such as when turned on by a user or when specific ventilation modes are in use.

As illustrated, method 200 includes a proximate monitoring operation 202. The ventilator during proximate monitoring operation 202 monitors one or more measurements of pressure and/or flow taken by a proximal sensor. As discussed above the proximal sensor is a sensor located at the proximate location. The proximate location is a location that is proximate or close to the patient in the ventilation tubing system, such as in or near a wye-fitting and/or a patient interface. In some embodiments, the proximate location is at the circuit wye. The monitoring operation 202 may monitor the measurements of the proximal sensor at a predetermined time or event, such as every breath, every computational cycle, every exhalation, every inhalation, every 5 ms, every 10 ms, every $5^{th}$ computational cycle, and etc. The predetermined time or event may be any suitable time or event for determining the internal leak flow of the ventilation tubing system. In some embodiments, net volume, tidal volume, inspiratory volume, and/or an expiratory volume are determined based on the senor output from the flow sensor and/or pressure sensor at the proximate location. Measurements taken by the proximal sensor or derived or estimated from measurements taken by the proximal sensor are referred to herein as proximate measurements, such as proximate flow, proximate pressure, and/or proximate volume. Any suitable module of the ventilator may perform proximate monitoring operation 202, such as the internal leak module, pneumatic system, total leak module, processor, and/or controller. The monitoring operation 202 may be performed as a normal part of the ventilator's operation regardless of whether the leak determination method 200 is being performed. Alternatively, the monitoring operation 202 may include additional functions related to obtaining, processing, and handling the sensor output that is not performed as part of normal ventilation.

Method 200 also includes an internal leak estimating operation 204. The ventilator during the internal leak estimating operation 204 estimate internal leak based at least the one or more measurements by the proximal sensor. In some embodiments, the ventilator during the internal leak estimating operation 204 determines the internal leak by performing a modeling operation and an estimating operation. The ventilator during the modeling operation of internal leak estimating operation 204, models internal leakage as a first internal leakage component through a first internal orifice of a fixed size and a second internal leakage component through a second internal orifice of a varying size using at least the one or more measurements by the proximal sensor. Next, the ventilator during the estimating operation of the internal leak estimating operation 204 estimates instantaneous internal leak flow of the breathing gas inhaled or exhaled by the patient based on the first internal leakage component, the second internal leakage component, and the one or more measurements by the proximal sensor. In some embodiments, the ventilator during the internal leak estimating operation 204 estimates an internal leak flow by utilizing the algorithm and listed equations discussed above for the internal leak module. Any suitable module of the ventilator may perform internal leak estimating operation 204, such as the internal leak module, pneumatic system, total leak module, processor, and/or controller.

In some embodiments, method 200 includes an airway monitoring operation 206 and a total leak estimating operation 208. In other embodiments, method 200 includes an airway monitoring operation 206, a total leak estimating operation 208, and an external leak estimating operation 210. In some embodiments, method 200 also includes a displaying operation 212.

The ventilator during the airway monitoring operation 206, monitors one or more measurements of pressure and/or flow by an inspiratory sensor and/or an expiratory sensor. In some embodiments, the ventilator during airway monitoring operation 206 determines an inspiratory pressure or flow based on the amount of inspiratory flow or pressure delivered or set to be delivered by the ventilator. Accordingly, the inspiratory sensor when referred to herein includes or covers measurements of inspiratory flow and/or pressure based on the delivered or set to be delivered pressure and/or flow by the ventilator The airway monitoring operation 206 may monitor the measurements of the inspiratory and/or expiratory sensor at a predetermined time or event, such as every breath, every computational cycle, every exhalation, every inhalation, every 5 ms, every 10 ms, every $5^{th}$ computational cycle, and etc. The predetermined time or event may be any suitable time or event for determining the total leak of the ventilation tubing system. In some embodiments, net volume, tidal volume, inspiratory volume, and/or an expiratory volume are determined based on the senor output from the inspiratory and/or expiratory sensor. Measurements taken by the inspiratory and/or expiratory sensor or derived or estimated from measurements taken by the inspiratory and/or expiratory sensor are referred to herein as airway measurements, such as airway flow, airway pressure, and/or airway volume. Any suitable module of the ventilator may perform airway monitoring operation 206, such as the internal leak module, pneumatic system, total leak module, processor, and/or controller.

The ventilator during total leak estimating operation 208 determines the total leak of the ventilation tubing system based at least on one or more measurements by the inspiratory sensor and/or the expiratory sensor. In some embodiments, the ventilator during the total leak estimating operation 208 estimates the total leak by performing a total modeling operation and a total estimating operation. The ventilator during the total modeling operation of total leak estimating operation 208 models total leakage as a first total leakage component through a first circuit orifice of a fixed size and a second total leakage component through a second circuit orifice of a varying size using at least the one or more measurements by at least one of the inspiratory sensor and the expiratory sensor. Next, the ventilator during the total estimating operation of total leak estimating operation 208 estimates instantaneous total leak flow of the breathing gas inhaled or exhaled by the patient based on the first total leakage component, second total leakage component, and the one or more measurements by the inspiratory sensor and/or the expiratory sensor. In some embodiments, the ventilator during the total leak estimating operation 208 estimates the total leak by utilizing the algorithm and listed equations discussed above for the total leak module. Any suitable module of the ventilator may perform total leak estimating operation 208, such as the internal leak module, pneumatic system, total leak module, processor, and/or controller.

The ventilator during the external leak estimating operation 210 estimates an instantaneous external leak flow based on the instantaneous total leak flow and the instantaneous internal leak flow. The external leak flow is a function of the instantaneous total leak flow and the instantaneous internal leak flow. In some embodiments, the ventilator during the external leak estimating operation 210 estimates the external leak flow by subtracting the internal leak flow from the total leak flow. In other embodiments, the ventilator during the external leak estimating operation 210 adjusts the total leak flow and the internal leak flow to account for the errors and signal delays of each of the different sensors and ventilator components utilized to determine the internal leak flow and total leak flow before estimating the external leak flow.

In some embodiments, method 200 includes a displaying operation 212. The ventilator during the displaying operation 212 displays any suitable information for display on a ventilator. In some embodiments, the ventilator during displaying operation 212 displays total leak flow, averaged total leak flow, internal leak flow, averaged internal leak flow, external leak flow, and/or averaged external leak flow. In further embodiments, the ventilator during displaying operation 212 displays a graph, chart or list of total leak flow, averaged total leak flow, internal leak flow, averaged internal leak flow, external leak flow, and/or averaged external leak flow per a predetermined number of computational cycle(s) or per breath(s). In yet further embodiments, the ventilator during displaying operation 212 displays event detection or ventilation treatment options based on the comparison of the internal leak flow and/or the total leak flow to predetermined thresholds. For example, the ventilator during displaying operation 212 may display a tube or patient circuit disconnect notice. Any suitable module of the ventilator may perform displaying operation 212, such as the display module, display, graphical user interface, remote monitor, and/or etc.

While the operations of method 200 are displayed in a specific order, these operations may be performed in any suitable order for estimating internal leak flow, total leak flow and/or external leak flow. For example, the proximate monitoring operation 202 and the airway monitoring operation 206 may be performed simultaneously or may overlap in performance. In further examples, the internal leak estimating operation 204 and the total leak estimating operation 208 may be performed simultaneously or may overlap in performance after the proximate monitoring operation 202 and the airway monitoring operation 206 are performed.

In further embodiments, the ventilator during the external leak estimating operation 210 compares the internal leak flow, total leak flow and/or external leak flow or function thereof to a threshold to determine proper ventilation, events, or conditions. For example, the external leak flow may be compared to a disconnect threshold to determine if the patient circuit has been disconnected from the patient interface or the patient. In other embodiments, the ventilator during the external leak estimating operation 210 compares the ratio of internal leak flow (or other factors such as leaked volume during inhalation) to total leak flow (or other factors such as total delivered volume during inhalation) to a disconnect threshold to determine if the if the patient circuit has been disconnected from the patient interface or the patient. For example, in some embodiments, the ventilator during the external leak estimating operation 210 determines that the patient circuit has been disconnected from the patient interface or the patient when the ratio of internal leak flow to total leak flow is greater than some user selected or manufacturer determined threshold. In another example, in some embodiments, the ventilator during the external leak estimating operation 210 determines that the patient circuit has been disconnected from the patient interface or the patient when the ratio of internal leak flow to total leak flow is greater than 90 percent and the total leak flow is above a predetermined threshold.

In some embodiments, if the ventilator during the external leak estimating operation 210 determines a condition, event, or improper ventilation based on the comparison of the internal leak flow, total leak flow and/or external leak flow or functions thereof to a threshold, the ventilator will issue an audio of visual notification of the detected condition, event, or improper ventilation. In some embodiments, the ventilator during displaying operation 212 displays the notification of the detected condition, event, or improper ventilation. For example, in some embodiments, the ventilator during displaying operation 212 displays the notification of a detected tube or patient circuit disconnection. In alternative embodiments, if the ventilator during the external leak estimating operation 210 determines a condition, event, or improper ventilation based on the comparison of the internal leak flow, total leak flow and/or external leak flow or functions thereof to a threshold, the ventilator will automatically change one or more ventilator settings, such flow, pressure, breath type, etc. to correct, prevent, modify, or reduce the detected condition, event, or improper ventilation.

In further embodiments, method 200 also includes a compensating operation 214. The ventilator during the compensating operation 214 adjusts the flow, pressure and/or volume measurements based on the internal leak flow, total leak flow and/or external leak flow. The ventilator then utilizes the adjusted flow, pressure and/or volume measurements during the compensating operation 214 in other calculations, event detections, condition detections, patient monitoring, and/or ventilation monitoring. For example, the leak adjusted flow, pressure and/or volume measurements may be utilized to determine resistance, compliance, triggering, and/or patient effort or muscle pressure during compensating operation 214. In other examples, the leak adjusted flow, pressure and/or volume measurements may be utilized by different breath types by the ventilator to determine inspiration, expiration, and/or the amount of pressure and/or flow to deliver during the compensating operation 214.

In some embodiments, a microprocessor-based ventilator that accesses a computer-readable medium, which can be transitory or non-transitory, having computer-executable instructions for performing the method of detecting leakage during ventilation is disclosed. This method includes repeatedly performing all or a portion of the steps disclosed in method 200 as described above and as illustrated in FIG. 2 with the modules as described above and/or as illustrated in FIG. 1.

In some embodiments, the ventilator system includes means for performing all or a portion of the steps disclosed in method 200 as described above and as illustrated in FIG. 2. The means for performing these embodiments are illustrated in FIG. 1 and described above.

Figure 3:
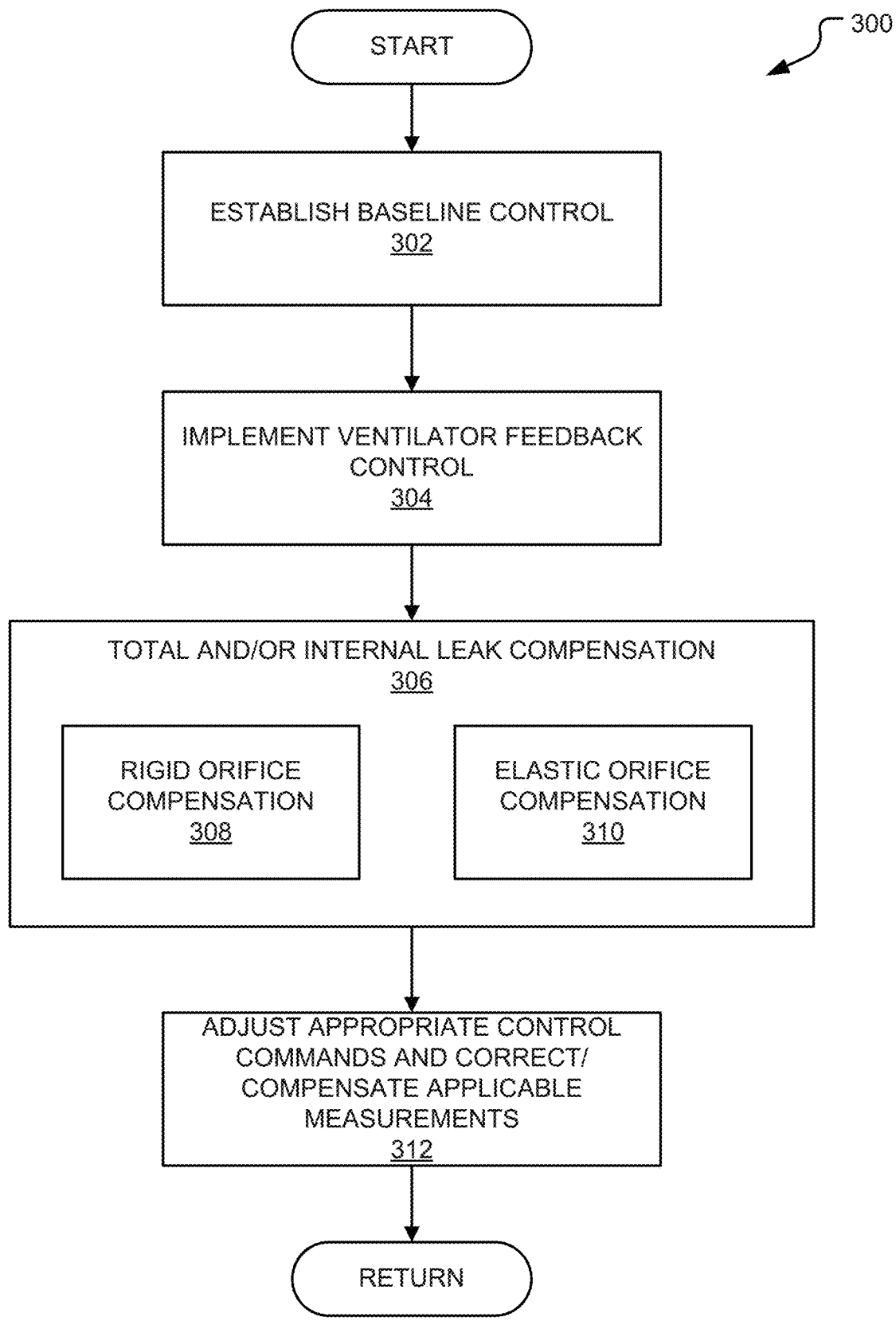
FIG. 3 illustrates an embodiment of a method for controlling a ventilator and includes a method for compensating for leaks in ventilator components.

FIG. 3 illustrates an embodiment of an exemplary control strategy 300 that may be implemented by the controller 110 or any other suitable component of the ventilator to increase the accuracy and timing of the baseline breathing assistance provided by ventilator 100 and pneumatic system 102 for a variety of respiratory therapies. In this example, the strategy is repeated periodically every breathing cycle. In other examples, the dynamic updating of leak estimation may occur more or less than once per patient breathing cycle.

At block 302, the routine establishes a baseline level of leak estimation and compensation. This may be a preset value stored in the controller 110 or may be updated taking into account various parameters of the breathing cycle and ventilator 100, such as the Positive End Expiratory Pressure PEEP, the set inspiratory pressure or flow/volume targets, the volumetric airflow delivered by pneumatic system 102, and type of the breathing circuit 131, etc.

Figure 4:
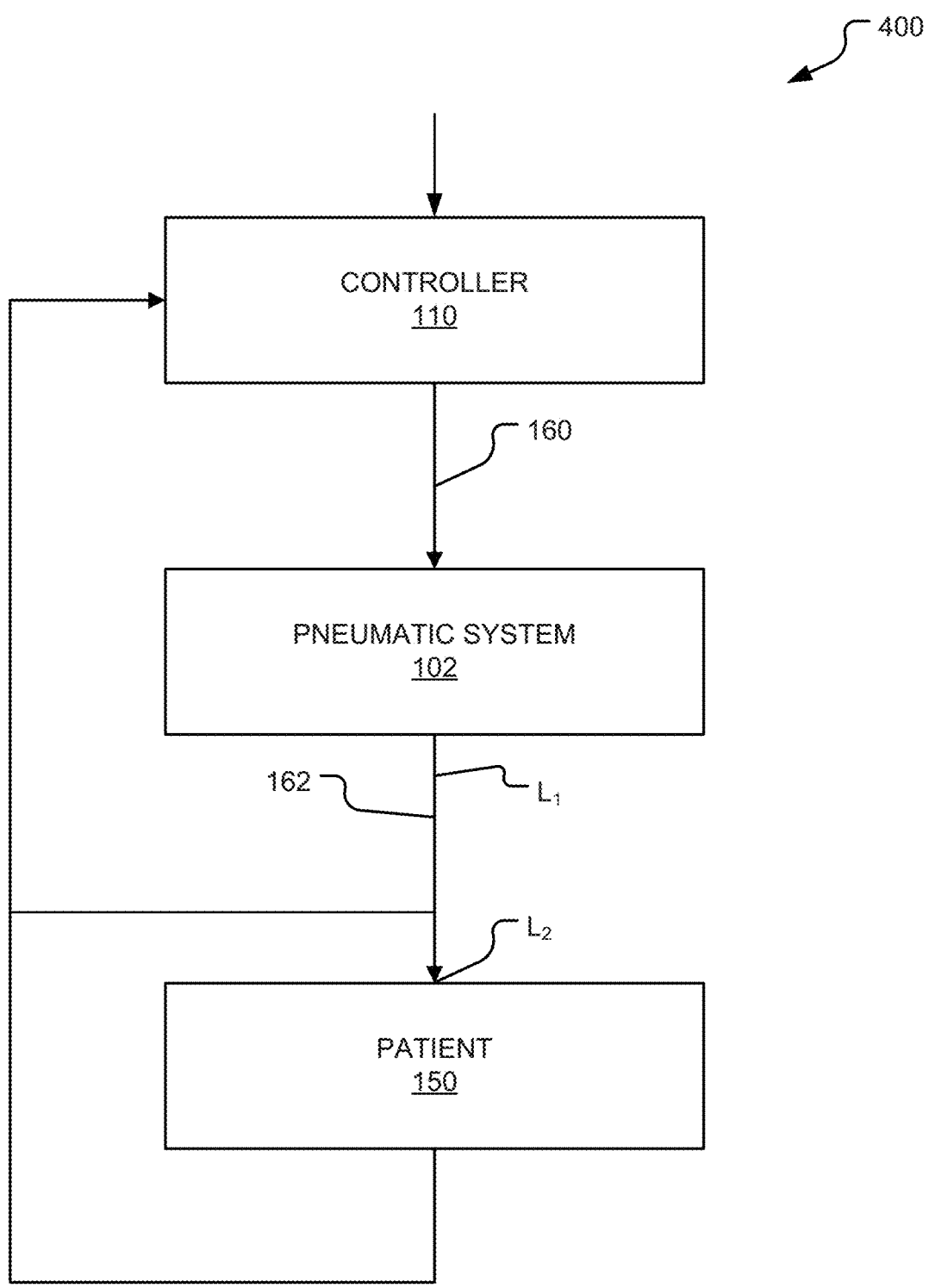
FIG. 4 illustrates an embodiment of a schematic representation of a control system employed by a ventilator.

The routine then proceeds to block 304 where the feedback control (e.g., as shown in FIG. 4) is implemented. Various control regimes may be implemented, including pressure) volume and/or flow regulation. Control may also be predicated on inputs received from the patient, such as pressure variations in the breathing circuit which indicate commencement of inspiration. Inputs applied via operator interface 120 may also be used to vary the particular control regime used. For example, the ventilator may be configured to run in various different operator-selectable modes, each employing different control methodologies.

The routine advances to block 306 where the total and/or internal leak flow compensation is performed. Various types of leak compensation may be implemented. For example, as shown at block 308, rigid-orifice compensation may be employed using values calculated as discussed above. In particular, holes or other leak sources may be present in non-elastic parts of the breathing circuit, such as the ports of a facial mask (not shown) and/or in the inspiratory and expiratory limbs. EQ #1 may be used to calculate the volumetric airflow through such an orifice for total leak, assuming the leak factor/resistance/conductance is constant. EQ #15 may be used to calculate the volumetric airflow through such an orifice for internal leak flow, assuming the leak factor/resistance/conductance is constant.

Depending on the model or models used to calculate the various leak flows, elastic properties of ventilator components may also be accounted for during total and/or internal leak flow compensation, as shown at block 310, for example using values calculated as described above. Specifically, elastic properties of patient interface 180 and/or breathing circuit 131 may be established (e.g., derived based on material properties such as elastic modulus, Poisson's ratio, etc.), and employed in connection with total leak calculations such as those discussed above in reference to EQ #6, 10 and/or 13, to account for the deformation of an elastic orifice. Additionally, elastic properties of patient interface 180 and/or breathing circuit 131 may be established (e.g., derived based on material properties such as elastic modulus, Poisson's ratio, etc.), and employed in connection with internal leak flow calculations such as those discussed above in reference to EQ #19, 22 and/or 24, to account for the deformation of an elastic orifice. Using these example calculations, constants $K_{y1}$ and $K_{y2}$ may be solved for and updated dynamically to improve the accuracy of leak estimation. In alternate implementations, the strategy may use any suitable alternate mechanism or models for taking into account the elastic properties of a ventilator component having a leak-susceptible orifice.

The routine then proceeds to block 312 where appropriate baseline control commands and measurements are adjusted to compensate for the leaks in the ventilator calculated in 306 i.e., adjust appropriate control command and correct and/or compensate applicable measurements. In many settings, it will be desirable to regularly and dynamically update the compensation level (e.g., once every breathing cycle) in order to optimize the control and compensation.

FIG. 4 schematically depicts exemplary control scheme of ventilator control 400. As shown, controller 110 issues control commands 160 to drive the pneumatic system 102 and thereby circulate breathing gas to and from patient 150. The depicted schematic interaction between pneumatic system 102 and patient 150 may be viewed in terms of pressure and/or flow "signals." For example, signal 162 may be an increased pressure which is applied to the patient via inspiratory limb 132. Control commands 160 are based upon inputs received at controller 110 which may include, among other things, inputs from operator interface 120, and feedback from pneumatic system 102 (e.g., from pressure/flow sensors) and/or sensed from patient 150.

In many cases, it may be desirable to establish a baseline pressure and/or flow trajectory for a given respiratory therapy session. The volume of breathing gas delivered to the patient's lung and the volume of the gas exhaled by the patient are measured or determined, and the measured or predicted/estimated leaks are accounted for to ensure accurate delivery and data reporting and monitoring. Accordingly, the more accurate the leak estimation, the better the baseline calculation of delivered and exhaled volume as well as event detection (e.g., triggering and cycling phase transitions).

Regardless of the particular cause or nature of the underlying condition, ventilator 100 typically provides breathing assistance during inspiration and exhalation. During inspiration if there is a leak from the patient tubing 130 more flow is required (depending on the leak size and circuit pressure) to achieve the same pressure level compared to no leak condition. During exhalation, a portion of the volume exhaled by the patient may exit through the leak and be missed by the ventilator exhalation flow measurement subsystem. In many cases, the goal of the control system is to deliver a controlled and known pressure or flow profile or trajectory (e.g., pressure or flow as a function of time) during the inspiratory phases of the breathing cycle to the patient's lungs. In other words, control is performed to achieve a desired time-varying pressure or flow output or signal 162 from pneumatic system 102, with an eye toward causing or aiding the desired tidal breathing at the patient's lung regardless of the leaks in the system.

Improper leak accounting can compromise the timing and magnitude of the control signals applied from controller 110 to pneumatic system 102 especially during volume delivery. Also, lack or inaccurate leak compensation can jeopardize spirometry and patient data monitoring and reporting calculations. As shown at schematic leak location $L_1$ and/or leak location $L_2$, the pressure applied from the pneumatic system 102 to patient interface 180 may cause leakage of breathing gas to atmosphere or within the patient. This leakage may occur, for example, at some point on inspiratory limb 132 or expiratory limb 134, or at where breathing circuit 131 couples to patient interface 180 or pneumatic system 102.

It is typical for some amount of breathing gas to escape via internal leak and via external leak. In facial masks, internal leaks can occur at a variety of locations around the edge of the mask, and the size and deformability of the mask can create significant leak variations. Under varying pressures, during inspiration and expiration orifice of $L_1$ (external leak) and/or $L_2$ (internal leak) may deform, altering the size of the leak orifice. Furthermore, the patient may shift (e.g., talk or otherwise move facial muscles), altering the size of leak orifice. Due to the elastic nature of some leaks and the movement of the patient, a leak compensation strategy assuming a constant size leak orifice and a size-varying or elastic leak orifice is necessary.

Accurately accounting for the relative magnitudes of leak $L_1$ and/or $L_2$ and differentiating between the two may provide significant advantages. In order for controller 110 to command the pneumatic system 102 to deliver the desired amount of volume/pressure to the patient at the desired time and measure/estimate the accurate amount of gas volume exhaled by the patient, the controller must have knowledge of how large leak $L_1$ and/or $L_2$ is during operation of the ventilator. The fact that the leak magnitude changes dynamically during operation of the ventilator introduces additional complexity to the problem of leak modeling.

For example, triggering and cycling (patient-ventilator) synchrony may also be compromised by sub-optimal leak estimation. In devices with patient-triggered and patient-cycled modalities that support spontaneous breathing efforts by the patient, it can be important to accurately detect when the patient wishes to inhale and exhale. Detection commonly occurs by using accurate pressure and/or lung flow (flow rates into or out of the patient lung) variations. leak $L_1$ and/or $L_2$ represents a leak in the airway that causes an error in the signals to the sensors of pneumatic system 102. This error may impede the ability of ventilator to detect the start of an inspiratory effort, which in turn compromises the ability of controller 110 to drive the pneumatic system in a fashion that is synchronous with the patient's spontaneous breathing cycles. Other examples of calculations and parameters affected by improper leak detections include the estimation of resistance, the estimation of compliance, and/or the estimation of patient effort (or muscle pressure).

Those skilled in the art will recognize that the methods and systems of the present disclosure may be implemented in many manners and as such are not to be limited by the foregoing exemplary embodiments and examples. In other words, functional elements being performed by a single or multiple components or modules, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components or modules, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces of modules and other components, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method of determining leakage during ventilation of a patient, comprising:
   delivering a flow of breathing gases to the patient via a ventilation tubing system including a patient interface;
   receiving output indicative of at least one of a flow measurement and a pressure measurement from sensors that are operatively coupled to the ventilation tubing system, the sensors including a proximal sensor and at least one of an inspiratory sensor or an expiratory sensor;
   estimating internal leak flow by modeling internal leakage through a first internal orifice of fixed size and a second internal orifice of varying size using the sensor output from at least the proximal sensor; and
   estimating total leak flow by modeling total leakage in the ventilation tubing system through a first circuit orifice of fixed size and a second circuit orifice of varying size using the sensor output from at least one of the inspiratory sensor or the expiratory sensor.

2. The method of claim 1, further comprising:
   displaying the internal leak flow and the total leak flow.

3. The method of claim 1, further comprising:
   calculating a ratio of the internal leak flow to the total leak flow.

4. The method of claim 3, further comprising:
   comparing the ratio to a disconnect threshold; and
   based on the comparing, detecting whether a disconnection exists in the ventilation tubing system.

5. The method of claim 4, further comprising:
   when the disconnection is detected, displaying a disconnect notification.

6. The method of claim 1, further comprising:
   based on the internal leak flow, detecting an error in at least one of the flow measurement or the pressure measurement; and
   adjusting at least one of the flow measurement or the pressure measurement.

7. The method of claim 1, further comprising:
   based on the internal leak flow, detecting an error in a calculated volume; and
   adjusting the calculated volume.

8. The method of claim 1, further comprising:
   detecting at least one of a condition or an event based on a comparison of the internal leak flow to a threshold.

9. The method of claim 1, further comprising:
   detecting improper ventilation based on a comparison of the internal leak flow to a threshold.

10. A method of determining leakage during ventilation of a patient, comprising:
    delivering a flow of breathing gases to the patient via a ventilation tubing system including a patient interface;

receiving output indicative of at least one of a flow measurement and a pressure measurement from sensors that are operatively coupled to the ventilation tubing system, the sensors including a proximal sensor and at least one of an inspiratory sensor or an expiratory sensor;

estimating internal leak flow by modeling internal leakage through a first internal orifice of fixed size and a second internal orifice of varying size using the sensor output from at least the proximal sensor;

estimating total leak flow by modeling total leakage in the ventilation tubing system through a first circuit orifice of fixed size and a second circuit orifice of varying size using the sensor output from at least one of the inspiratory sensor or the expiratory sensor; and estimating an external leak flow based on the internal leak flow and the total leak flow.

11. The method of claim 10, further comprising:
displaying one or more of the internal leak flow, the external leak flow, or the total leak flow.

12. The method of claim 10, further comprising:
calculating a ratio of the internal leak flow to the total leak flow.

13. The method of claim 12, further comprising:
comparing the ratio to a disconnect threshold; and
based on the comparing, detecting whether a disconnection exists in the ventilation tubing system.

14. The method of claim 13, further comprising:
when the disconnection is detected, displaying a disconnect notification.

15. The method of claim 10, further comprising:
based on the internal leak flow, detecting an error in at least one of the flow measurement or the pressure measurement; and
adjusting at least one of the flow measurement or the pressure measurement.

16. The method of claim 10, further comprising:
based on the internal leak flow, detecting an error in a calculated volume; and
adjusting the calculated volume.

17. The method of claim 10, further comprising:
detecting at least one of a condition or an event based on a comparison of the internal leak flow to a threshold.

18. The method of claim 10, further comprising:
detecting improper ventilation based on a comparison of the internal leak flow to a threshold.

19. A method of determining leakage during ventilation of a patient, comprising:
delivering a flow of breathing gases to the patient via a ventilation tubing system including a patient interface;
receiving output indicative of at least one of a flow measurement and a pressure measurement from sensors that are operatively coupled to the ventilation tubing system, the sensors including a proximal sensor and at least one of an inspiratory sensor or an expiratory sensor;
estimating internal leak flow by modeling internal leakage through a first internal orifice of fixed size and a second internal orifice of varying size using the sensor output from at least the proximal sensor;
estimating total leak flow by modeling total leakage in the ventilation tubing system through a first circuit orifice of fixed size and a second circuit orifice of varying size using the sensor output from at least one of the inspiratory sensor or the expiratory sensor;
calculating a ratio of the internal leak flow to the total leak flow; and
based on the ratio, determining that a disconnection exists in the ventilation tubing system.

* * * * *